United States Patent
Alsberg et al.

(10) Patent No.: US 8,273,373 B2
(45) Date of Patent: Sep. 25, 2012

(54) PHOTOCROSSLINKED BIODEGRADABLE HYDROGEL

(75) Inventors: Eben Alsberg, Cleveland, OH (US); Oju Jeon, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 177 days.

(21) Appl. No.: 12/649,700

(22) Filed: Dec. 30, 2009

(65) Prior Publication Data

US 2011/0008443 A1    Jan. 13, 2011

Related U.S. Application Data

(60) Provisional application No. 61/141,266, filed on Dec. 30, 2008.

(51) Int. Cl.
- *A61K 9/14* (2006.01)
- *A61K 31/12* (2006.01)
- *A01N 35/00* (2006.01)
- *A61M 31/00* (2006.01)

(52) U.S. Cl. .................. 424/484; 514/675; 604/500
(58) Field of Classification Search .................. 424/484
See application file for complete search history.

(56) References Cited

OTHER PUBLICATIONS

Ohta et al., "Novel heparin/alginate gel combined with basic fibroblast growth factor promotes nerve regeneration in rat sciatic nerve", 2004, Journal of Biomedical Materials Research, vol. 71A, pp. 661-668.*

* cited by examiner

*Primary Examiner* — Gina C Yu
*Assistant Examiner* — Michael B Pallay
(74) *Attorney, Agent, or Firm* — Tarolli, Sundheim, Covell & Tummino LLP

(57) ABSTRACT

A photocrosslinked biodegradable hydrogel includes a plurality of natural polymer macromers cross-linked with a plurality of hydrolyzable acrylate cross-links. The hydrogel is cytocompatible and produces substantially non-toxic products upon degradation.

24 Claims, 25 Drawing Sheets

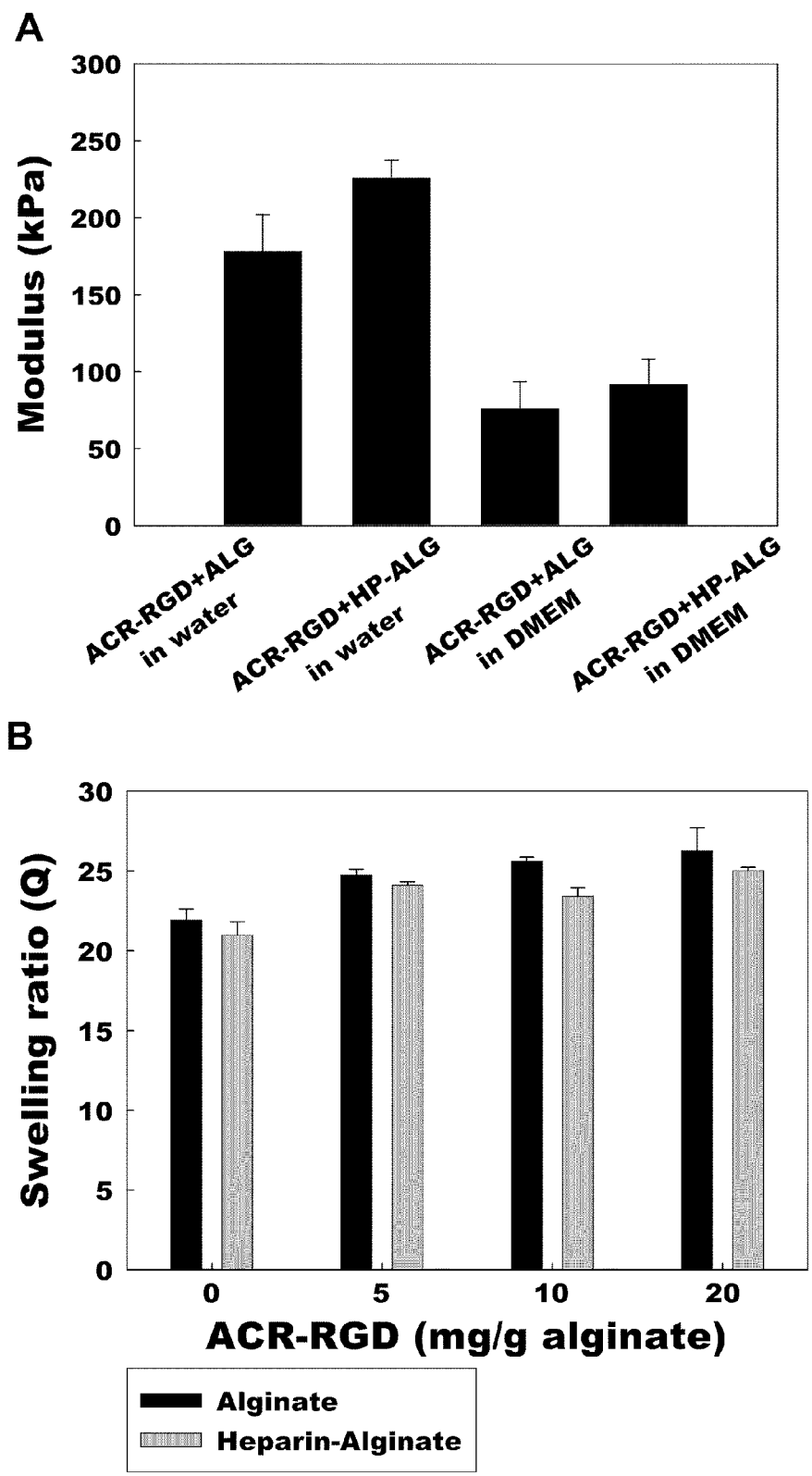
Fig. 5A-B

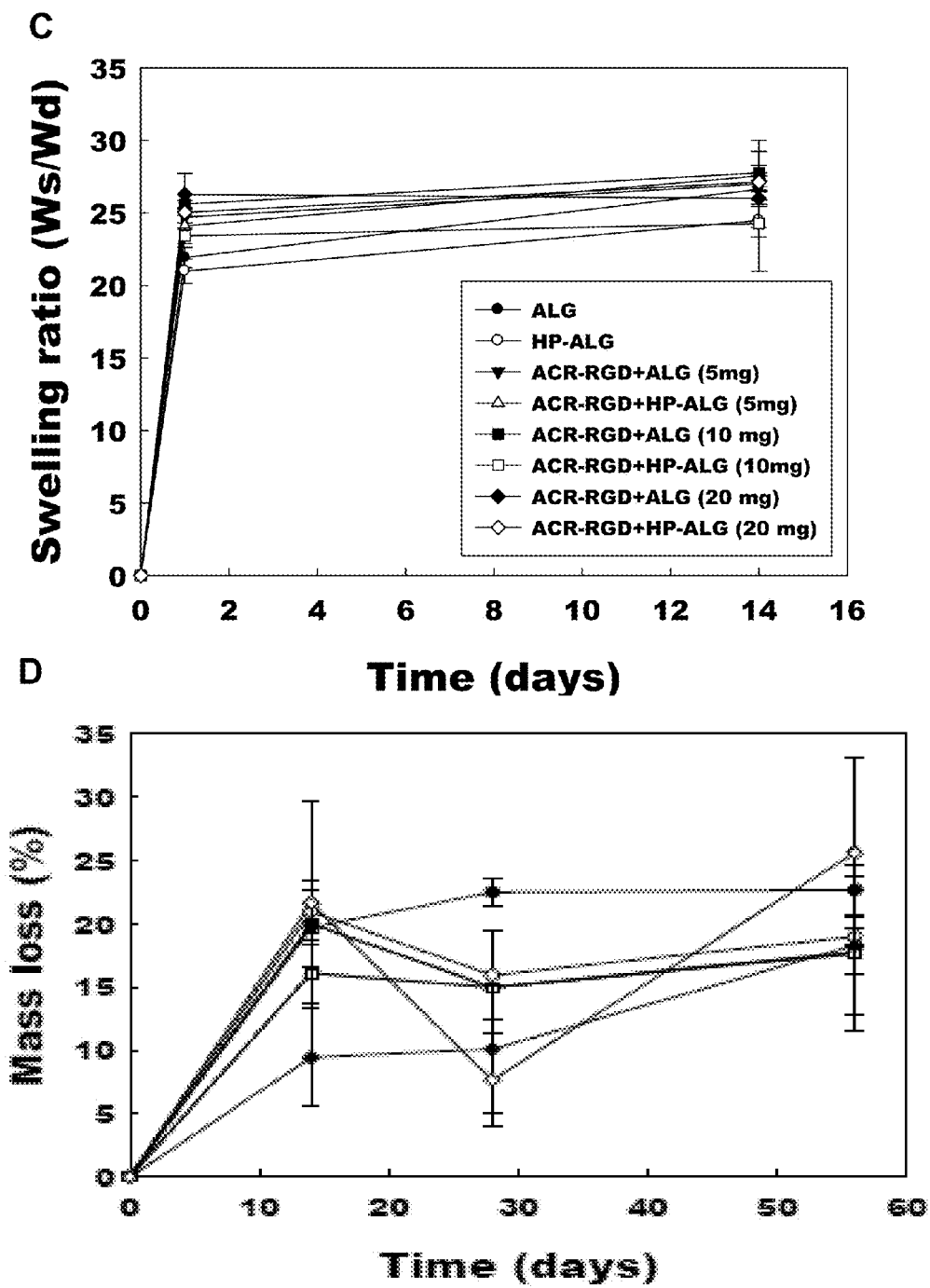
Figs. 5C-D

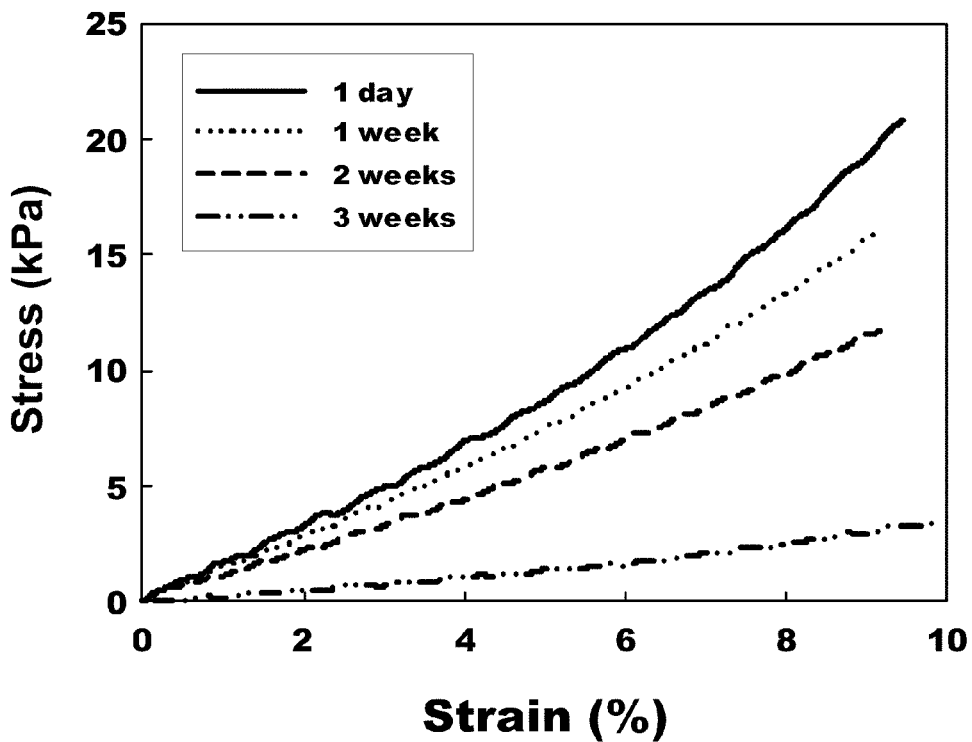
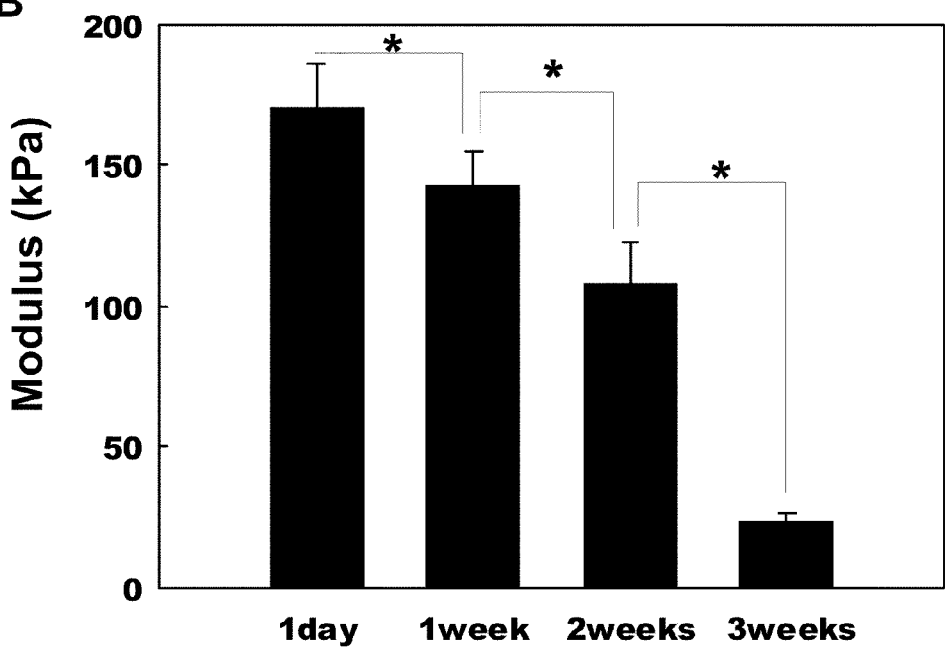
Figs. 12A-B

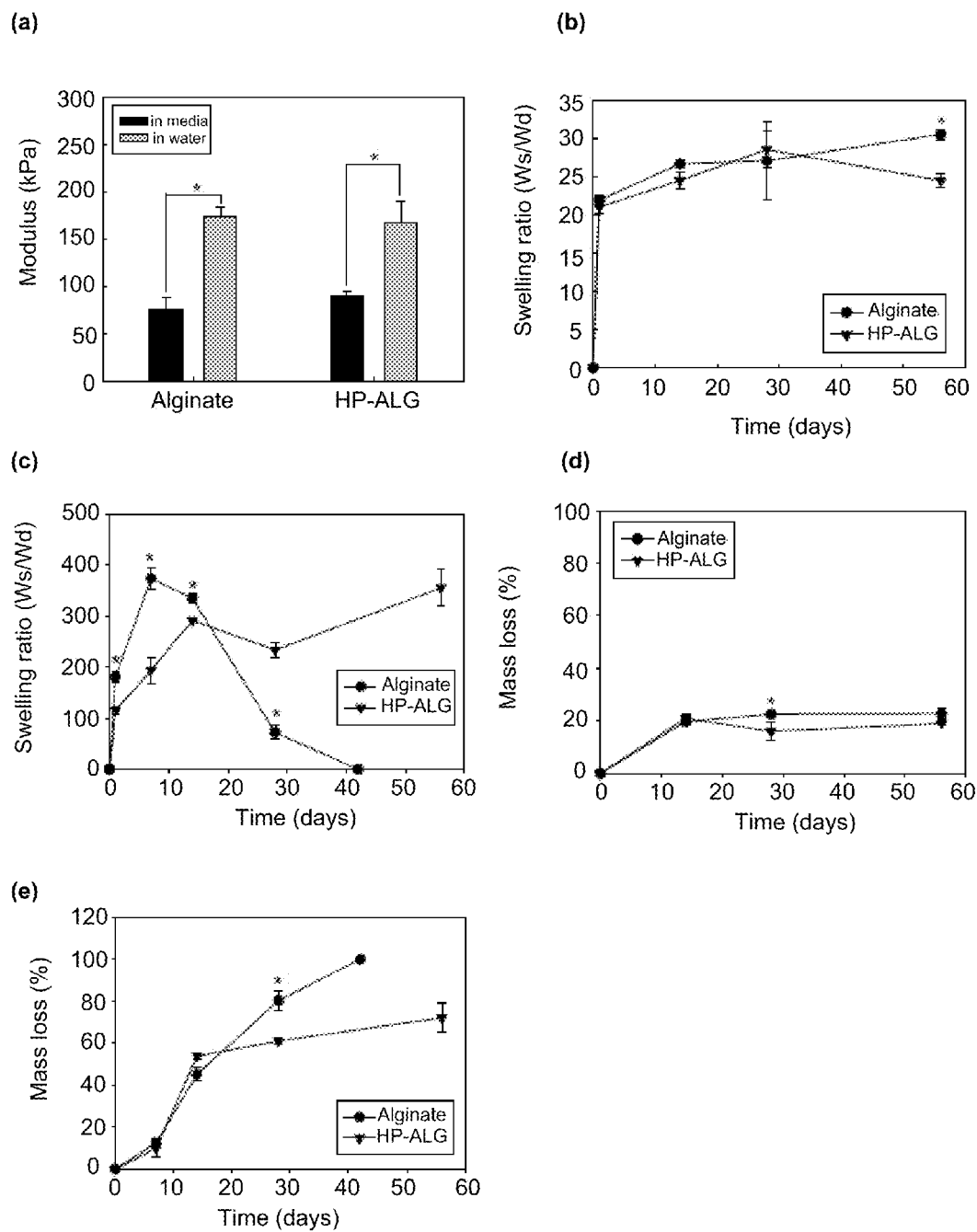
Figs. 15a-e

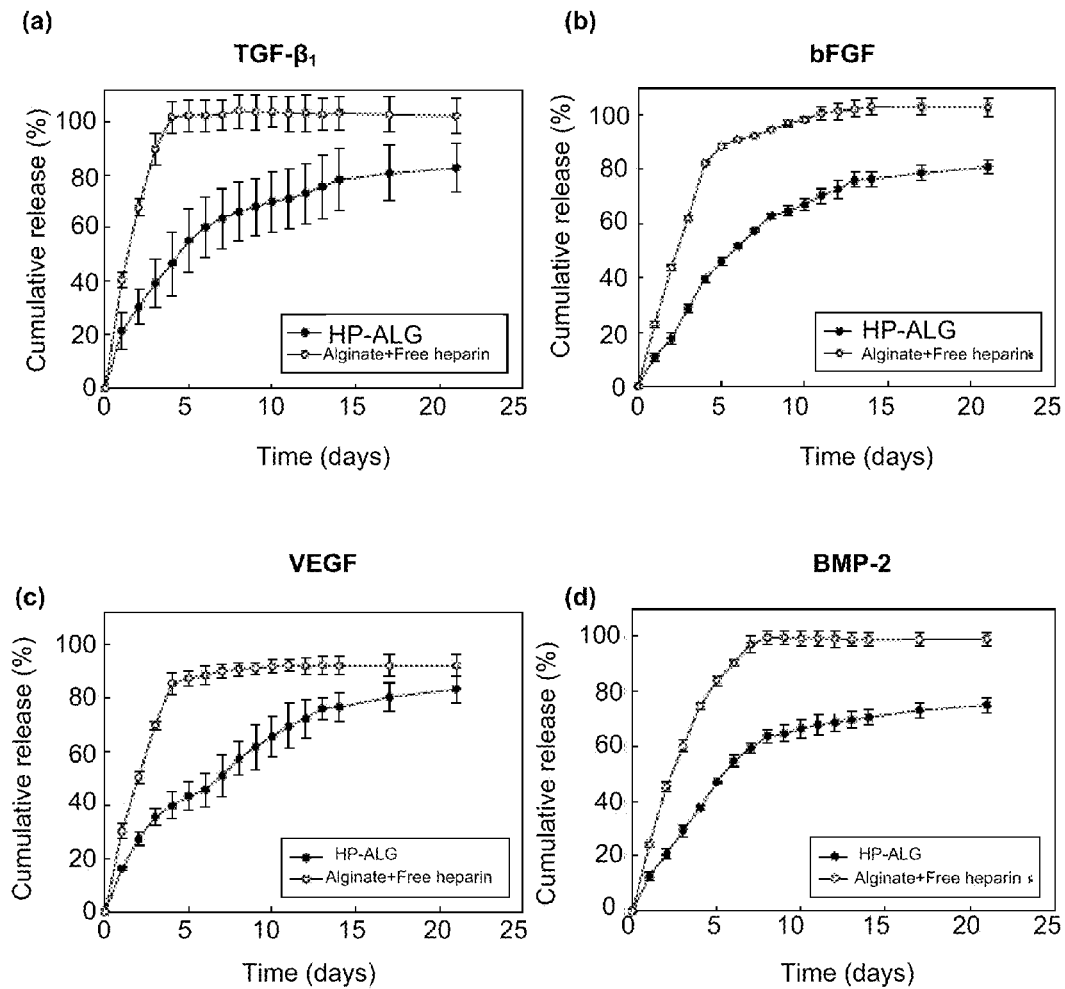
Figs. 16a-d

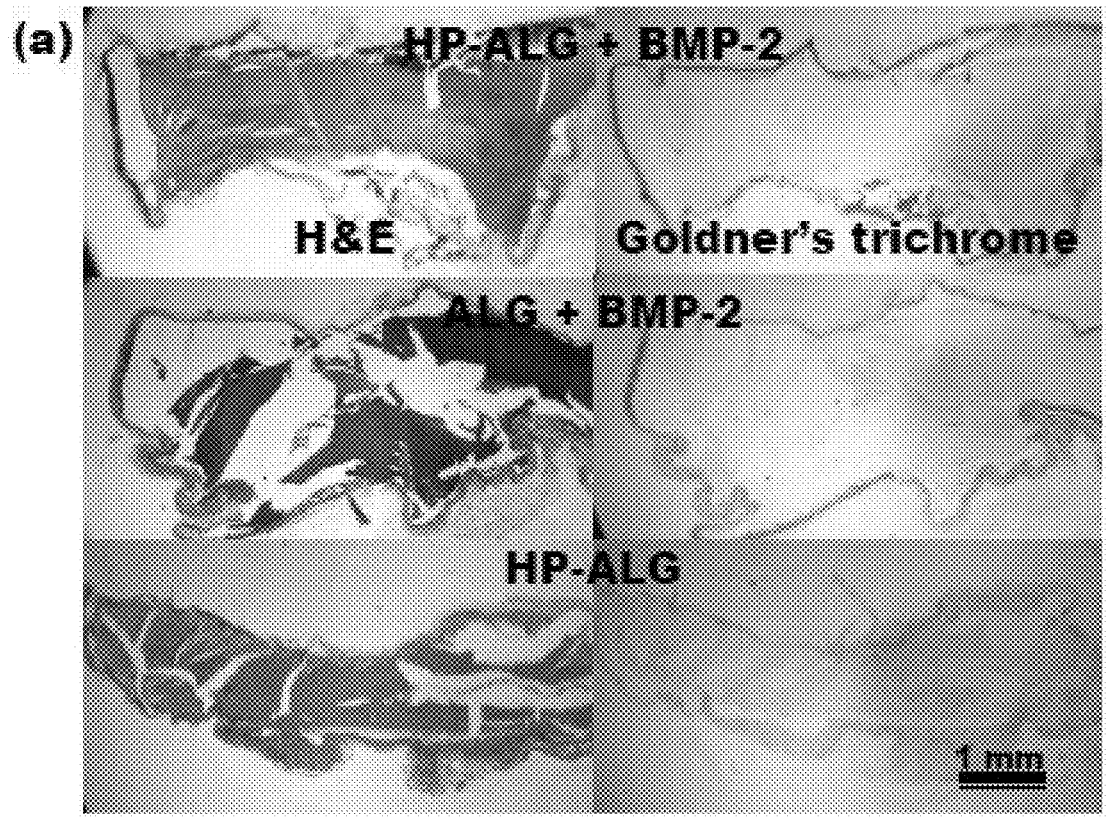
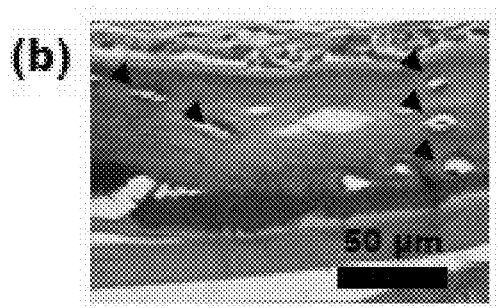
Figs. 18a-b

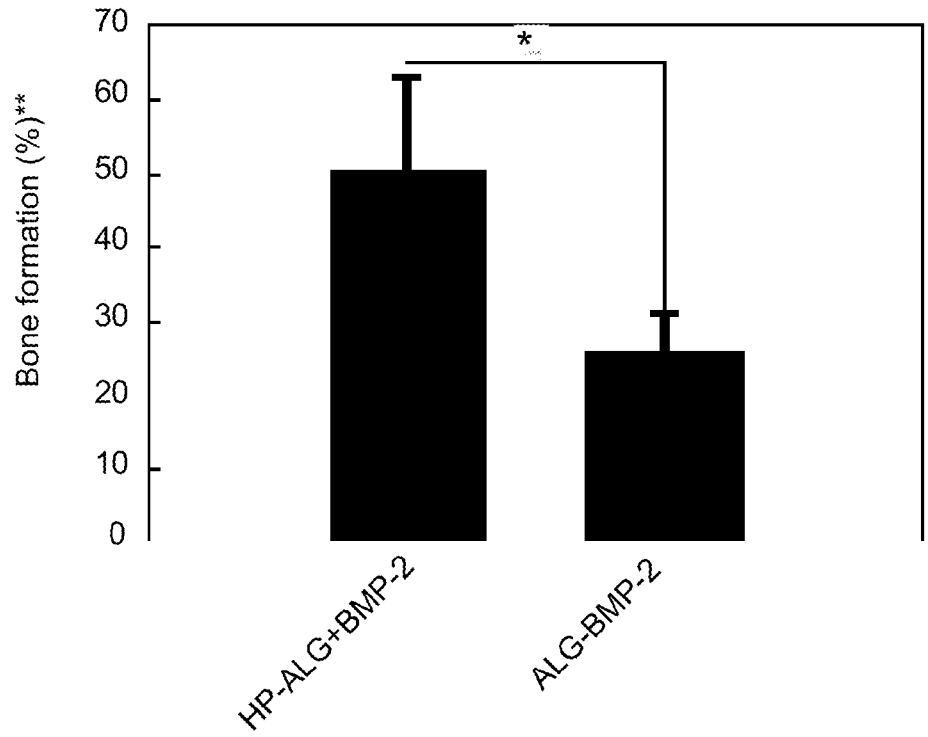
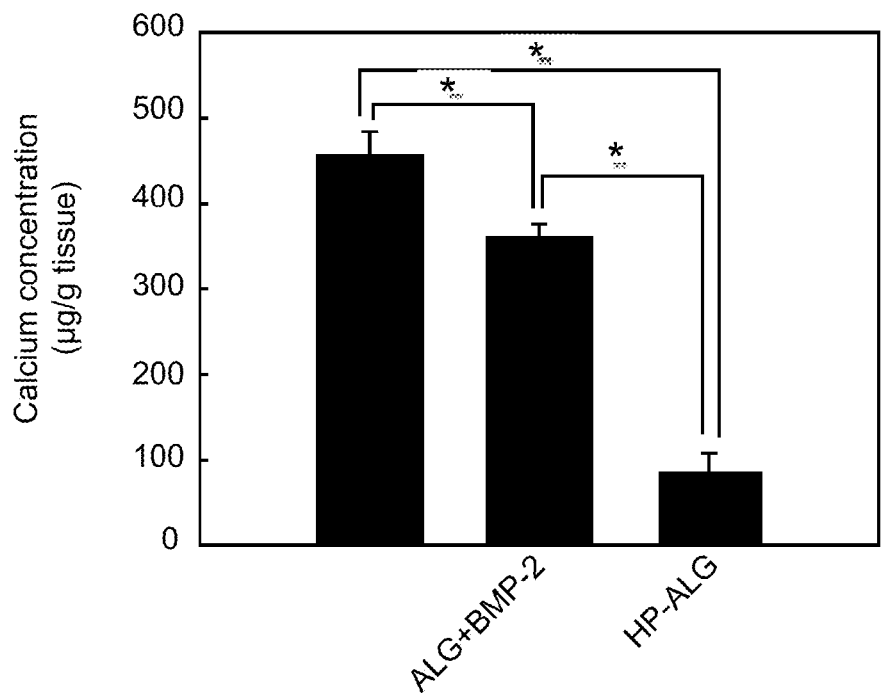
Figs. 19a-b

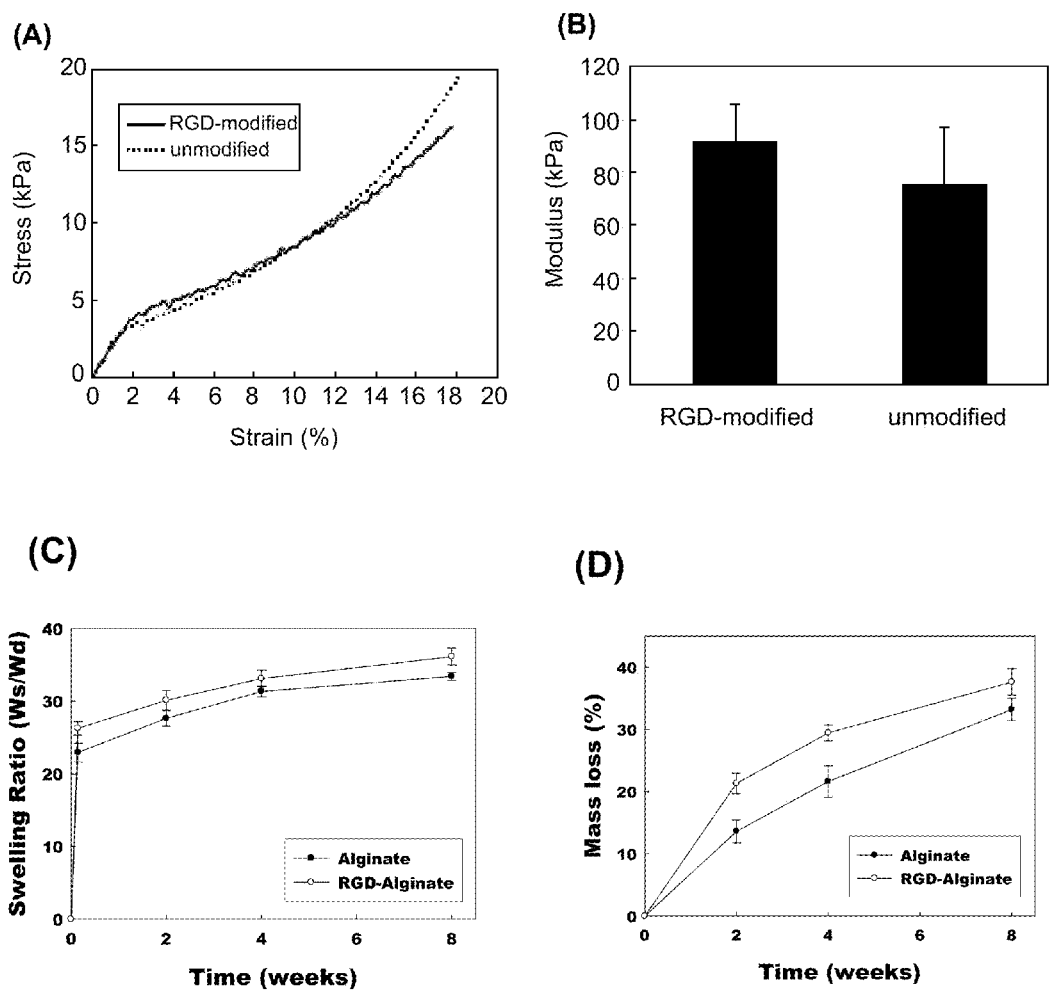
Figs. 20A-D

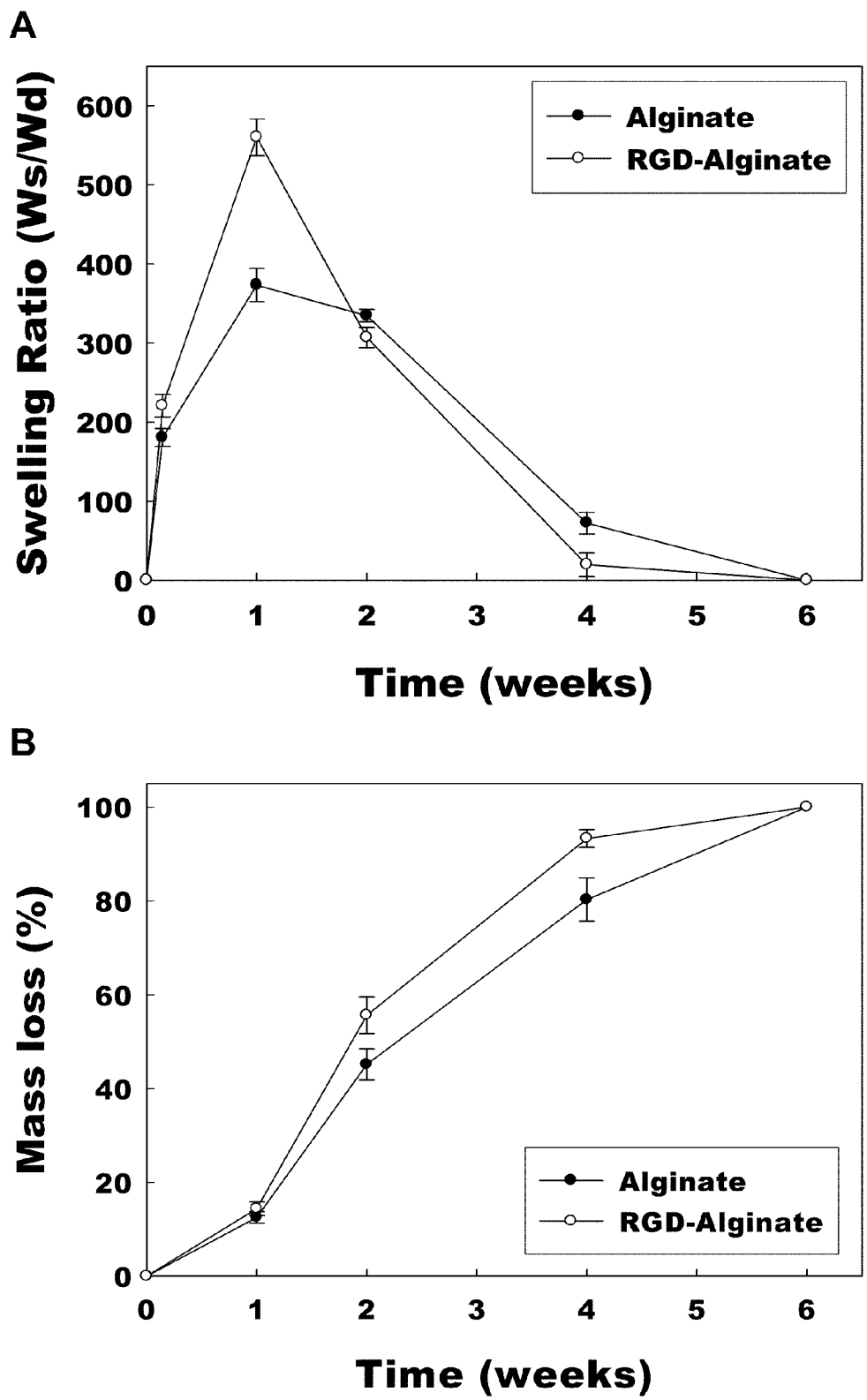
Figs. 21A-B

PHOTOCROSSLINKED BIODEGRADABLE HYDROGEL

RELATED APPLICATION

This application claims priority from U.S. Provisional Patent Application No. 61/141,266, filed Dec. 30, 2008, the entirety of which is hereby incorporated by reference.

TECHNICAL FIELD

The present invention generally relates to tissue engineering, bioactive factor delivery, and disease therapeutics, and more particularly to a photocrosslinked biodegradable hydrogel.

BACKGROUND OF THE INVENTION

Hydrogels are used in biomedical applications, such as drug delivery vehicles, cell encapsulation matrices, and tissue engineering scaffolds because many of their physical properties are similar to natural tissue. Hydrogels are insoluble 3-D networks of physically or chemically cross-linked hydrophilic polymers, which exhibit a high degree of swelling in aqueous environments.

Alginate is a linear unbranched polysaccharide derived from seaweed that contains the repeating units of 1,4-linked β-D-mannuronic acid and α-L-guluronic acid. Alginates have reversible gelling properties in aqueous solutions related to the ionic interactions between divalent cations. Alginate can be formed into a hydrogel and used as a drug delivery vehicle.

There is limited control over the mechanical properties, swelling ratios, and degradation profiles of ionically cross-linked alginate hydrogels, which is likely due to the uncontrollable loss of divalent cations into the surrounding environment. Approaches to chemically crosslinking alginate microcapsules or macroscopic hydrogels may utilize intermolecular covalent cross-linking rather than ionic cross-linking in order to synthesize alginate hydrogels with a wide range of mechanical properties. However, the reagents and reaction conditions used with such approaches can be toxic to encapsulated cells or growth factors, and hydrogels covalently cross-linked are not biodegradable.

SUMMARY OF THE INVENTION

The present invention generally relates to tissue engineering, and more particularly to a photocrosslinked biodegradable hydrogel, a method for forming the hydrogel, and related methods for using the hydrogel in different tissue engineering application. The photocrosslinked biodegradable hydrogel can include a plurality of natural polymer macromers cross-linked with a plurality of degradable cross-links. The hydrogel can be cytocompatible and produce substantially non-toxic products upon degradation.

Another aspect of the present invention relates to a method for forming a photocrosslinked biodegradable hydrogel. The method can include reacting at least one acryl group with at least one natural polymer macromer to form a mixture comprising a plurality of acrylated macromers. The mixture can then be contacted with a photoinitiator that can initiate cross-linking of the macromers. The mixture can be exposed to a light source to initiate cross-linking of the macromers and form a plurality of natural polymer macromers cross-linked with a plurality of hydrolyzable acrylate cross-links.

A further aspect of the invention relates to a method for promoting tissue growth in a subject. The method can include administering a photocrosslinked biodegradable hydrogel to a target site in the subject. The hydrogel can include a plurality of natural polymer macromers cross-linked with a plurality of hydrolyzable acrylate cross-links and at least one cell dispersed on or within the hydrogel. The hydrogel may be cytocompatible and produce substantially non-toxic products upon degradation.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 5A-D are a series of plots showing: elastic modulus in compression of photocrosslinked acrylated RGD+methacrylated alginate (ACR-RGD-ALG) or acrylated RGD+MA-Heparin+methacrylated alginate (ACR-RGD-HP-ALG) hydrogel after 24 hrs equilibration in deionized water or DMEM (10 mg acrylated RGD/g alginate) (FIG. 5A); equilibrium swelling ratios of photocrosslinked ALG and HP-ALG with various amount of acrylated RGD after 24 hours equilibration in DMEM (FIG. 5B); swelling ratio change of photocrosslinked ACR-RGD-ALG or acrylated ACR-RGD-HP-ALG hydrogel in DMEM over time (FIG. 5C); and degradation of photocrosslinked ACR-RGD-ALG or acrylated ACR-RGD-HP-ALG hydrogel in DMEM over time (FIG. 5D);

FIGS. 12A-B are plots comparing stress vs. strain (FIG. 12A) and elastic moduli vs. time in compression of photocrosslinked MAALG-25 hydrogels during degradation (FIG. 12B) (*p<0.05);

FIGS. 15A-E are a series of plots showing elastic moduli in compression (FIG. 15A), swelling ratio changes in DMEM (FIG. 15B) and diH$_2$O (FIG. 15C), and in vitro degradation of photocrosslinked HP-ALG hydrogels and alginate hydrogels in DMEM (FIG. 15D) and diH$_2$O (FIG. 15E). Mass loss (%)=$(W_i-W_d)/W_i \times 100$, where $W_i$=initial weight and $W_d$=weight after degradation (values represent mean and standard deviation; *p<0.05 compared to HP-ALG);

FIGS. 16A-D are a series of plots showing TGF-$\beta_1$ (FIG. 16A), FGF-2 (FIG. 16B), VEGF (FIG. 16C), and BMP-2 (FIG. 16D) released from photocrosslinked HP-ALG hydrogels and alginate hydrogels (values represent mean±standard deviation; *p<0.05);

FIGS. 18A-B are a series of microscopic photographs showing H&E and Goldner's trichrome-stained histological sections of BMP-2 delivery system implants at 8 weeks (FIG. 18A) and H&E staining at high magnification of the BMP-2-loaded HP-ALG implant at 8 weeks (FIG. 18B). The mature bone in FIG. 23B contained viable osteocytes (closed triangle) (photographs in FIG. 18A were taken at the same magnification);

FIGS. 19A-B are a series of graphs showing bone formation vs. implant type (FIG. 19A) and calcium concentration vs. implant type (FIG. 19B) at 8 weeks after implantation (values represent mean±standard deviation; *p<0.05);

FIGS. 20A-D are a series of plots showing stress vs. strain (FIG. 20A), elastic moduli (FIG. 20B) in compression of RGD-modified and unmodified photocrosslinked alginate hydrogels after 24 hours equilibrium in DMEM, swelling ratios (FIG. 20C), and in vitro degradation (FIG. 20D) of RGD-modified and unmodified photocrosslinked alginate hydrogels in DMEM (*p<0.05);

FIGS. 21A-B are a series of plots showing swelling ratios (FIG. 22A) and in vitro degradation (FIG. 22B) vs. time of RGD-modified and unmodified photocrosslinked alginate hydrogels in diH$_2$O (*p<0.05);

DETAILED DESCRIPTION

Figure 1:
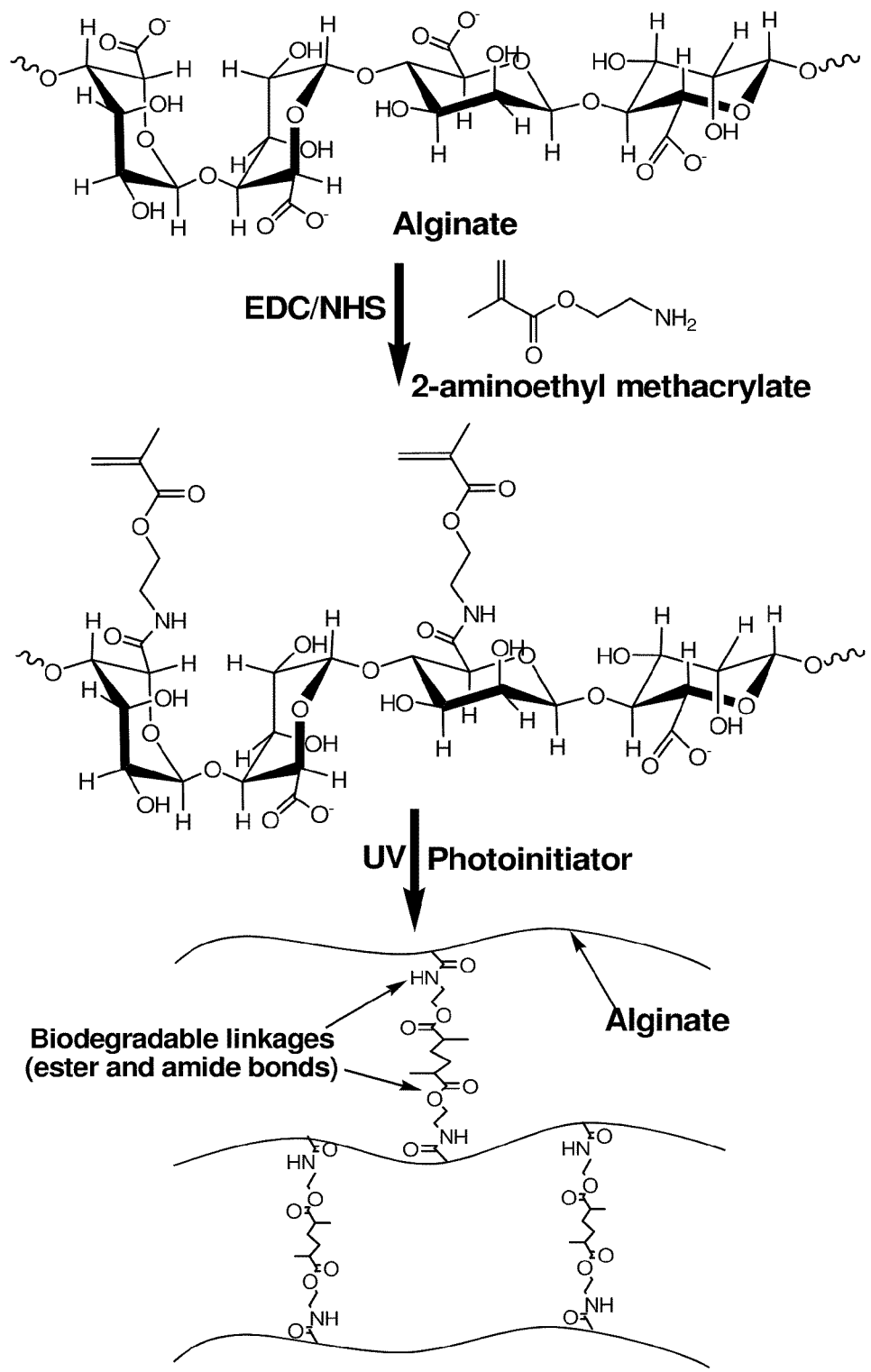
FIG. 1 is a schematic illustration showing a process for preparing a photocrosslinked degradable hydrogel in accordance with one aspect of the present invention.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "bioactive agent" can refer to any agent capable of promoting tissue formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-$\beta$ I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "carrier material" can refer to a material capable of transporting, releasing, and/or complexing at least one bioactive agent.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "aggregate" can refer to a group or cluster comprising at least two or more cells (e.g., progenitor and/or differentiated cells).

As used herein, the term "population" can refer to a collection of cells, such as a collection of progenitor and/or differentiated cells.

As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage.

The present invention generally relates to tissue engineering, and more particularly to a photocrosslinked biodegradable hydrogel, a method for forming the hydrogel, a method for using the hydrogel in different tissue engineering applications, a method for attaching heparin to control release of growth factors, and separate methods for incorporating cell adhesion peptides on or within the biodegradable hydrogel. The photocrosslinked biodegradable hydrogel of the present invention is substantially cytocompatible (i.e., substantially non-cytotoxic) and includes controllable physical properties, such as degradation rate, swelling behavior, and mechanical properties.

The photocrosslinked biodegradable hydrogel can include a plurality of natural polymer macromers cross-linked with a plurality of cross-links that are degradable after administration to a subject in vivo. The number or percentage of cross-links linking the macromers can be varied to control the mechanical properties, swelling ratios, and degradation profiles of the hydrogels. Degradation of the cross-links in vivo allows the hydrogel to more readily biodegrade and be used for in vivo applications. Additionally, as discussed in more detail below, the photocrosslinked biodegradable hydrogel can be used as a substrate for the incorporation and/or attachment of various agents and/or cells. The photocrosslinked biodegradable hydrogel can be injectable and/or implantable, and can be in the form of a membrane, sponge, gel, solid scaffold, spun fiber, woven or unwoven mesh, nanoparticle, microparticle, or any other desirable configuration.

In an aspect of the invention, the photocrosslinked biodegradable hydrogel can include at least on cross-link that can be hydrolyzed to allow degradation of the hydrogel in vivo. In one embodiment, the cross-link can include ester, amide, acetal, and/or ketal groups or linkages that can be readily hydrolyzed in vivo to promote degradation of the hydrogel. In one example, the hydrolyzable cross-link can include at least one hydrolyzable acrylate (e.g., methacrylate) cross-link. The hydrolyzable acrylate cross-link can include at least one hydrolyzable ester and/or hydrolyzable amide linkage. As explained further below, hydrolytic degradation of the hydrolyzable acrylate cross-link can create space for cell growth and deposition of a new extracellular matrix to replace the photocrosslinked biodegradable hydrogel in vivo.

An example of a biodegradable hydrogel with an acrylate cross-link with a hydrolyzable ester and/or amide linkage has the following Formula I:

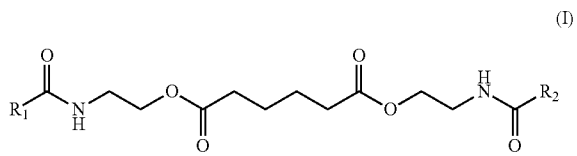

where $R_1$ and $R_2$ can comprise the same or different natural polymer macromers. The natural polymer macromers can be any natural polymer or oligomer that includes a functional group (e.g., a carboxylic group) that can be further polymerized. Examples of natural polymers or oligomers are saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose.

The hydrolyzable acrylate cross-link can be formed by reacting an acryl group (e.g., a methacryl group) with a natural polymer or oligomer to form a plurality of acryl substituted macromers. The acryl substituted macromers can then be combined with a cross-link initiator, such as a photoinitiator, and then cross-linked to promote formation of at least one hydrolyzable acrylate cross-link between the macromers.

In another example of the present invention, the photocrosslinked biodegradable hydrogel can have Formula II:

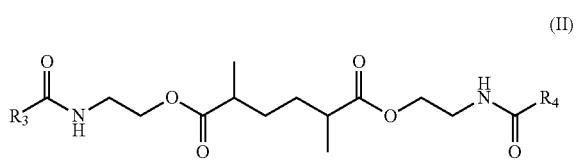

wherein each of $R_3$ and $R_4$ can include alginate main chains. As shown in FIG. 1, the photocrosslinked biodegradable hydrogel can comprise a plurality of alginate macromers cross-linked with a plurality of hydrolyzable methacrylate cross-links. The alginate can be obtained from a commercially available source, such as FMC BIOPOLYMER.

In another example of the present invention, the photocrosslinked biodegradable hydrogel can have Formula III:

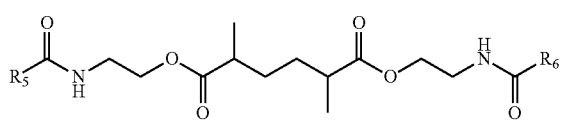

wherein $R_5$ can include an alginate main chain; a methacrylated alginate main chain; and/or an acrylated alginate main chain; and $R_6$ can include a heparin main chain; a methacrylated heparin main chain; and/or an acrylated heparin main chain. Alternatively, $R_6$ can comprise polypeptide, such as a cell adhesion ligand amino acid sequence (e.g., a mono-acrylate or mono-methacrylate cell adhesion sequence), a growth factor (e.g., a mono-acrylate or mono-methacrylate growth factor), a di-acrylate or di-methacrylate cell cleavable amino acid sequence (e.g., by enzymatic degradation), and the like.

The swelling behavior, mechanical properties, and degradation rates of the photocrosslinked biodegradable hydrogel can be controlled by changing the percentage of cross-links in the hydrogel. The percentage of cross-links can be varied between about 1% and about 50% by weight, and, for example, between about 4% and about 25% by weight. By increasing the percentage of cross-links, for example, the degradation rate of the photocrosslinked biodegradable hydrogel can be decreased. Additionally, the compressive stiffness of the photocrosslinked biodegradable hydrogel can be increased by increasing the percentage of cross-links. Further, the swelling behavior of the photocrosslinked biodegradable hydrogel can be increased by decreasing the percentage of cross-links.

Figure 2:
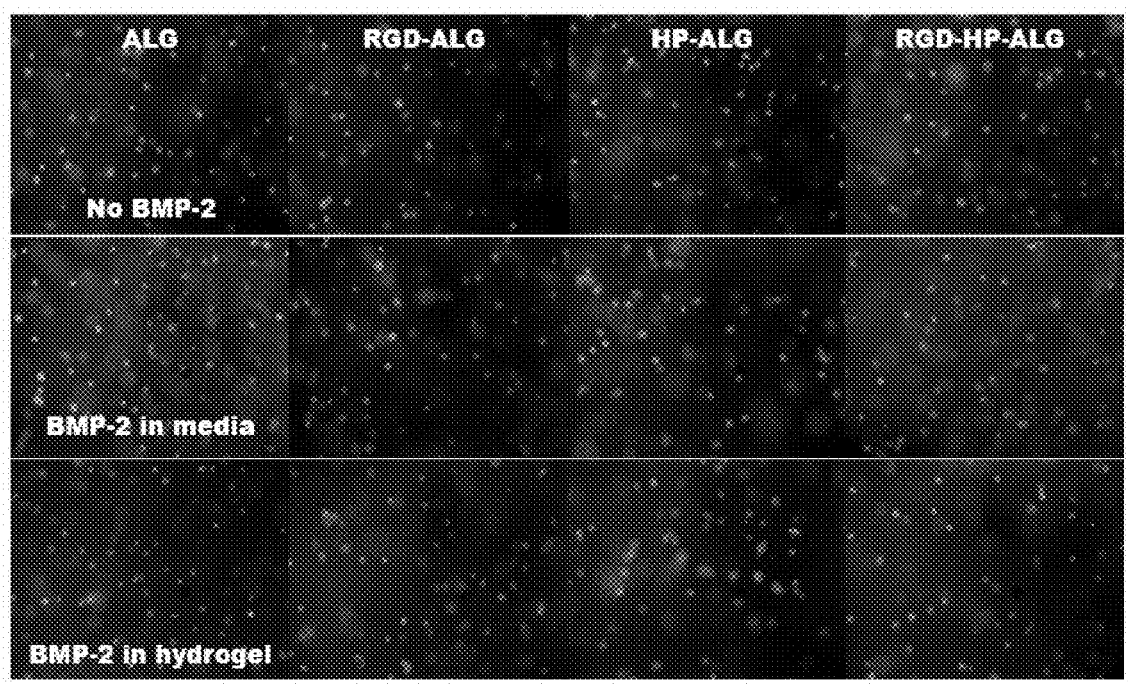
FIG. 2 is a series of fluorescent photographs of human MSCs photoencapsulated with BMP-2 using ALG, RGD-ALG, HP-ALG, and RGD-HP-ALG hydrogels after 2-weeks of culture.

In another aspect of the present invention, the photocrosslinked biodegradable hydrogel can include at least one cell dispersed on or within the hydrogel. For example, cells can be entirely or partly encapsulated within the photocrosslinked biodegradable hydrogel. Cells can include any progenitor cell, such as a totipotent stem cell, a pluripotent stem cell, or a multipotent stem cell, as well as any of their lineage descendant cells, including more differentiated cells (described above), such as $CD34^+$ MSCs. For example, human MSCs can be photoencapsulated using a heparin-modified, photocrosslinked biodegradable hydrogel (FIG. 2).

The cells can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into or onto the photocrosslinked biodegradable hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

In another aspect of the present invention, the photocrosslinked biodegradable hydrogel can include at least one attachment molecule to facilitate attachment of at least one cell thereto. The attachment molecule can include a polypeptide or small molecule, for example, and may be chemically immobilized onto the photocrosslinked biodegradable hydrogel to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences. It will be appreciated that the at least one attachment molecule may also improve cell attachment to microspheres, the incorporation of cells into the hydrogel, and hydrogel formation.

Figure 3:
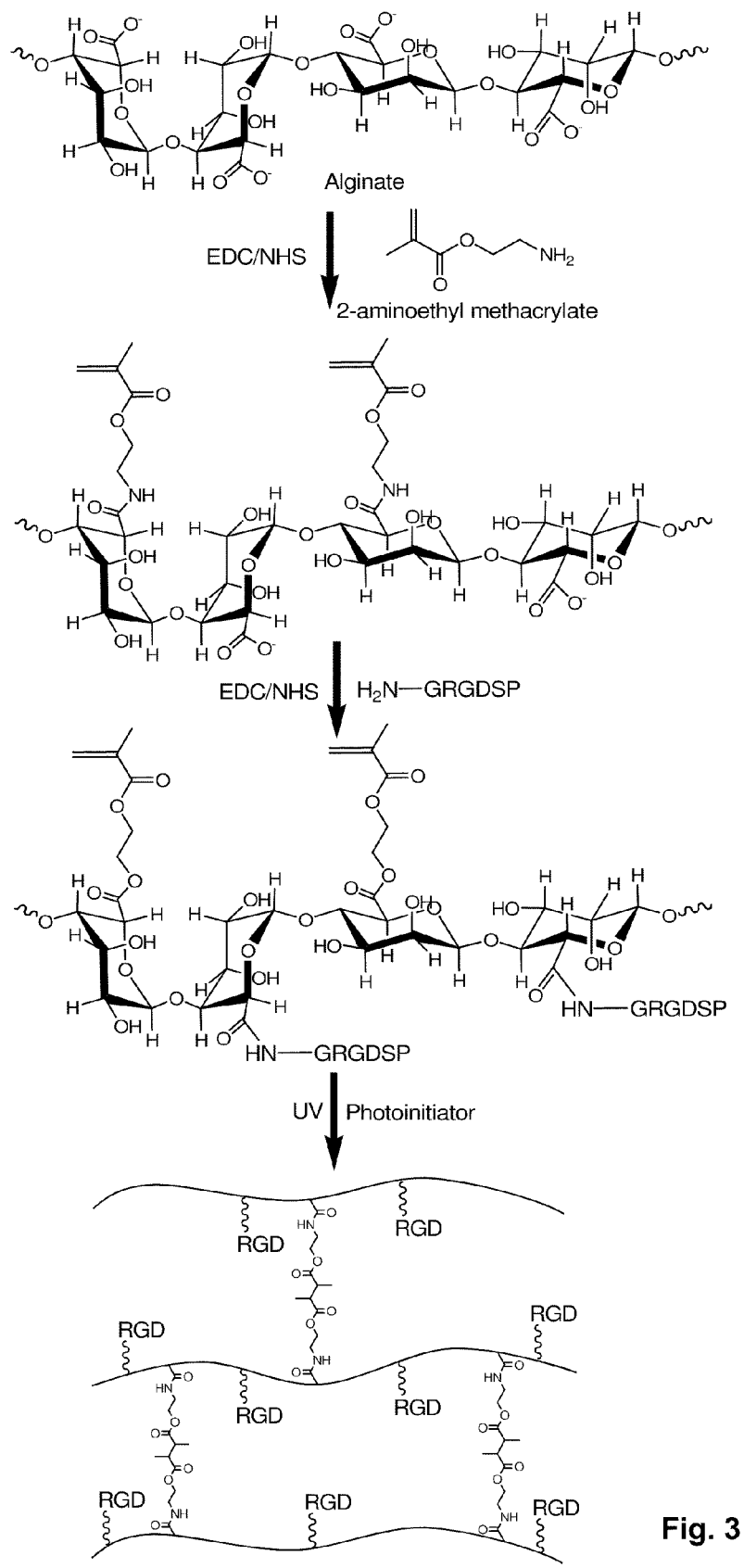
FIG. 3 is a schematic illustration showing a process for preparing an RGD-modified methacrylated alginate in accordance with an aspect of the invention.

In an example of the present invention, an attachment molecule can include a peptide having the amino acid sequence of SEQ ID NO: 1 that is chemically immobilized onto the photocrosslinked biodegradable hydrogel to facilitate cell attachment. As shown in FIG. 3, for example, EDC/NHS (carbodiimide) chemistry can be used to prepare methacrylated alginate modified with at least one attachment molecule having the amino acid sequence of SEQ ID NO: 1. The methacrylated alginate can then be cross-linked using a photoinitiator to form a biodegradable hydrogel.

Figure 4:
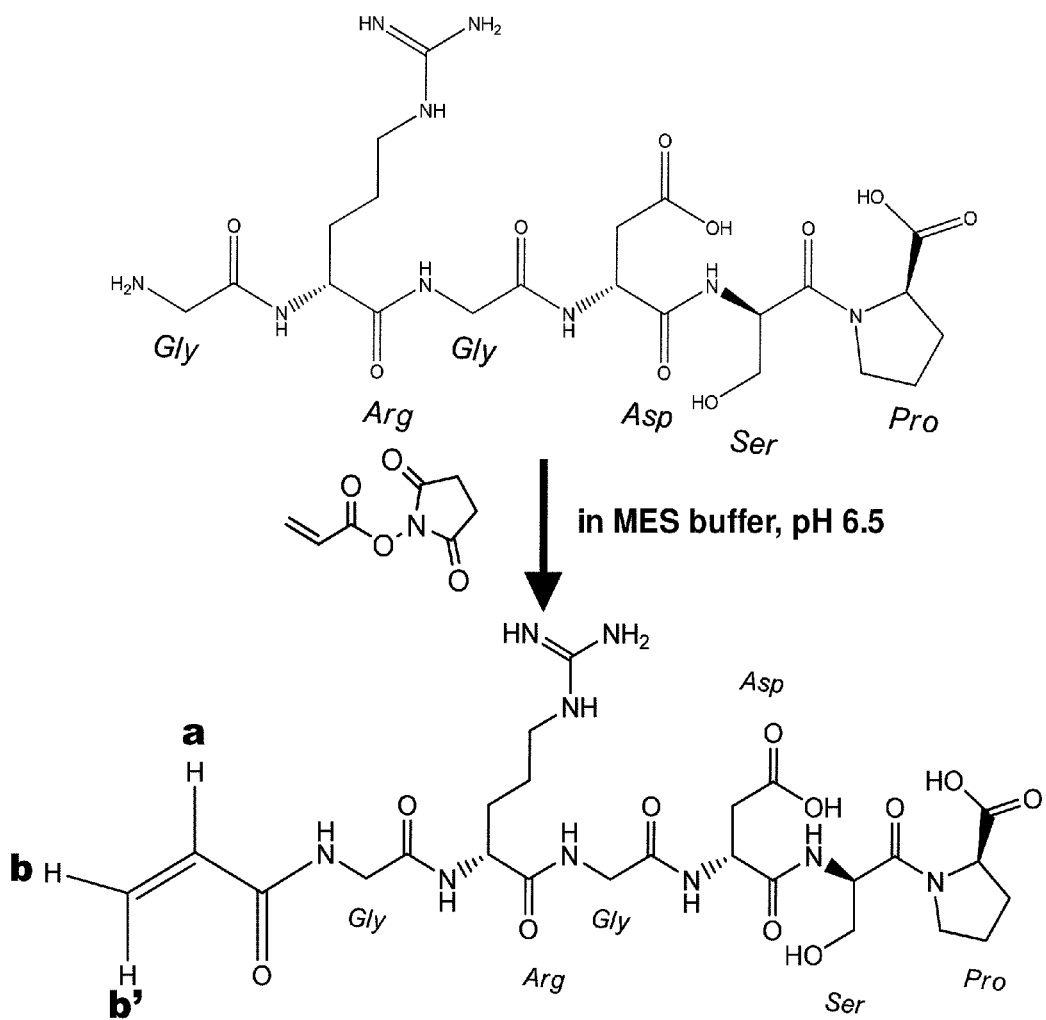
FIG. 4 is a schematic illustration showing the synthesis of an acrylated RGD-modified alginate hydrogel in accordance with another aspect of the invention.

Alternatively, the at least one attachment molecule can be chemically modified to include a moiety that can be used to couple the attachment molecule to the macromer. For example, at least one attachment molecule having the amino acid sequence of SEQ ID NO: 1 can be acrylated (e.g., methacrylated) as shown in FIG. 4. The acrylated attachment molecule can be cross-linked with the acrylate macromer to form a cross-linked biodegradable hydrogel. The acrylated attachment molecule can also be cross-linked with acrylated heparin and acrylated alginate to vary the mechanical properties of the hydrogel as shown in FIG. 5.

In another aspect of the present invention, the photocrosslinked biodegradable hydrogel can include at least one bioactive agent that is capable of modulating a function and/or characteristic of a cell. For example, the bioactive agent may be capable of modulating a function and/or characteristic of a cell that is dispersed on or within the photocrosslinked biodegradable hydrogel. Alternatively or additionally, the bioactive agent may be capable of modulating a function and/or characteristic of an endogenous cell surrounding a photocrosslinked biodegradable hydrogel implanted in a tissue defect, for example, and guide the cell into the defect.

The at least one bioactive agent can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

In another aspect of the present invention, the photocrosslinked biodegradable hydrogel can be modified or configured to differentially and/or controllably release at least one bioactive agent by forming at least one concentration gradient within the hydrogel. The hydrogel can have multiple gradients in the same hydrogel, and the gradients can run in the same or opposite directions. The gradients can be comprised of different components, such as different photo-alginates having different molecular weights or acrylation (e.g., methacrylation) percentages, methacrylated heparin, acrylated cell adhesion ligands, bioactive factors, cells, etc. As discussed below, for example, the photocrosslinked biodegradable hydrogel can be formed into a particular shape or form to facilitate release of one or more bioactive agents according to a gradient release profile. Alternatively, one or more materials or agents can be added to the photocrosslinked biodegradable hydrogel to facilitate differential and/or controlled release of one or more bioactive agents according to a gradient release profile.

In one example of the present invention, the photocrosslinked biodegradable hydrogel can be formed into alginate microbeads or microspheres capable of carrying and differentially and/or controllably releasing at least one bioactive agent. Alginate microspheres can be prepared by dissolving methacrylated alginate in an about 2% w/v solution in deionized water containing about 0.05% w/v photoinitiator (e.g., D-2959). About 10 ml of alginate solution can be added to 50 ml of iso-octane containing about 5% v/v Span 80. The resulting solution can then be emulsified by sonicating at about 40 W for about 30 seconds. Next, about 2.5 ml of about 30% v/v Tween 80 in water can be added as a surfactant, and the solution stirred for about 5 minutes. To ionically crosslink the microspheres, about 10 ml of filtered $CaCl_2$ (about 700 mM) can be added in a drop-wise fashion and then stirred for about 5 minutes. Next, about 50 ml of isopropanol can be added and the particles stirred for an additional period of time (e.g., about 5 minutes). The particles can then be collected by centrifuging at about 4000 RPM for about 5 minutes, followed by washing about 3 times with about 25 ml isopropanol. The particles can be air dried then resuspended in deionized water containing about 0.05% w/v photoinitiator (e.g., D-2959). The particles can then be photocrosslinked under UV light for about 10 minutes (if desired, the calcium can be removed at this point with about 1 M citric acid solution for 10 minutes), frozen, and lyophilized.

In another example of the present invention, a heparin-modified, photocrosslinked biodegradable hydrogel can be formed into microbeads or microspheres. As described in the example above, alginate microspheres can first be prepared. Next, methacrylated heparin can be added to the alginate solution (e.g., in a concentration of about 10% w/w to alginate). About 10 ml of alginate solution can be added to 50 ml of iso-octane containing about 5% v/v Span 80. The resulting solution can then be emulsified by sonicating at about 40 W for about 30 seconds. Next, about 2.5 ml of about 30% v/v Tween 80 in water can be added as a surfactant, and the solution stirred for about 5 minutes. To ionically crosslink the microspheres, about 10 ml of filtered $CaCl_2$ (about 700 mM) can be added in a drop-wise fashion and then stirred for about 5 minutes. Next, about 50 ml of isopropanol can be added and the particles stirred for an additional period of time (e.g., about 5 minutes). The particles can then be collected by centrifuging at about 4000 RPM for about 5 minutes, followed by washing about 3 times with about 25 ml isopropanol. The particles can be air dried then resuspended in deionized water containing about 0.05% w/v photoinitiator (e.g., D-2959). The particles can then be photocrosslinked under UV light for about 10 minutes (if desired, the calcium can be removed at this point with about 1 M citric acid solution for 10 minutes), frozen, and lyophilized.

Figure 6:
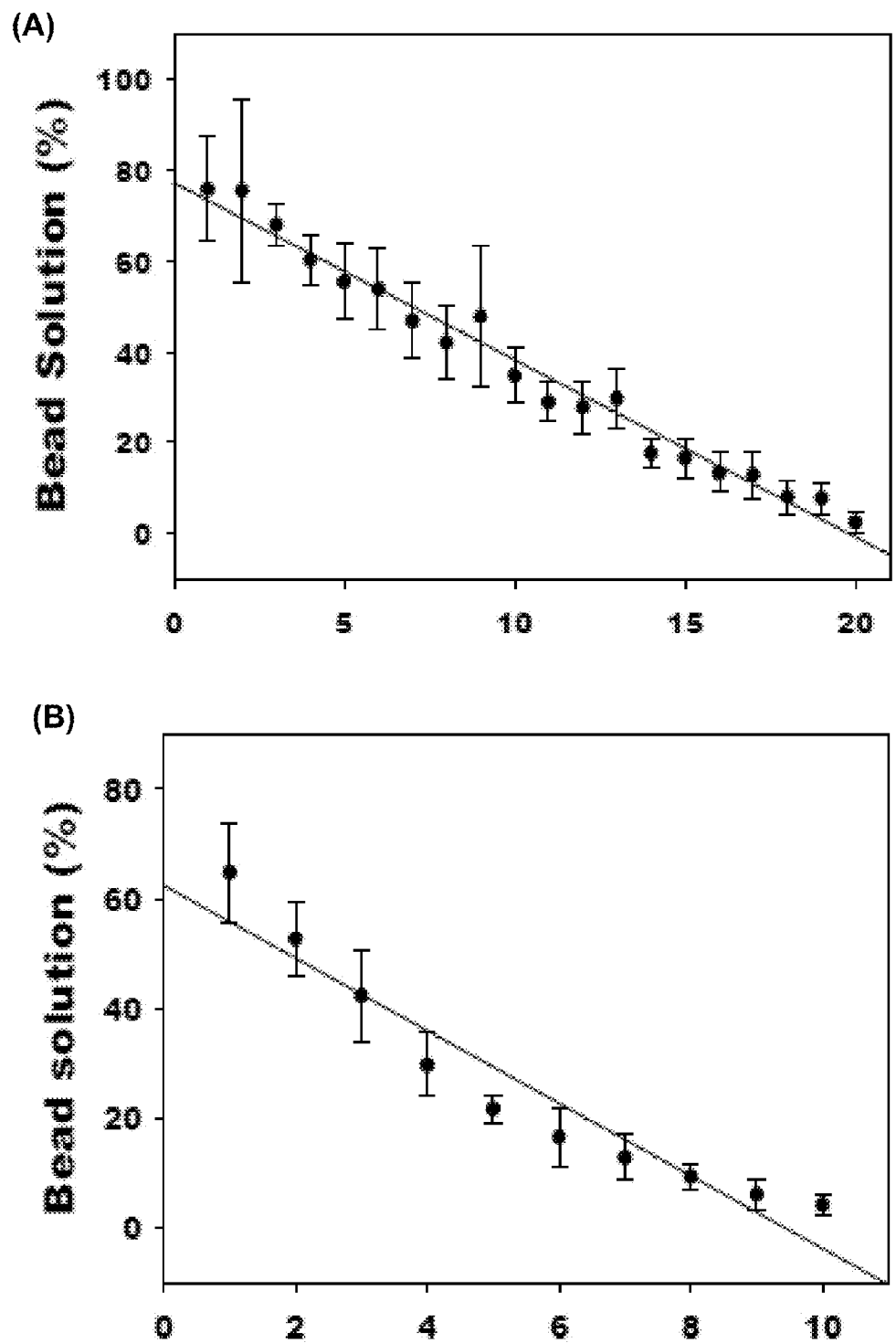
FIGS. 6A-B are a series of plots showing quantification of microbead gradient along 10 cm (FIG. 8A) and 5 cm (FIG. 8B) hydrogel (5 mm sections)
Figure 7:
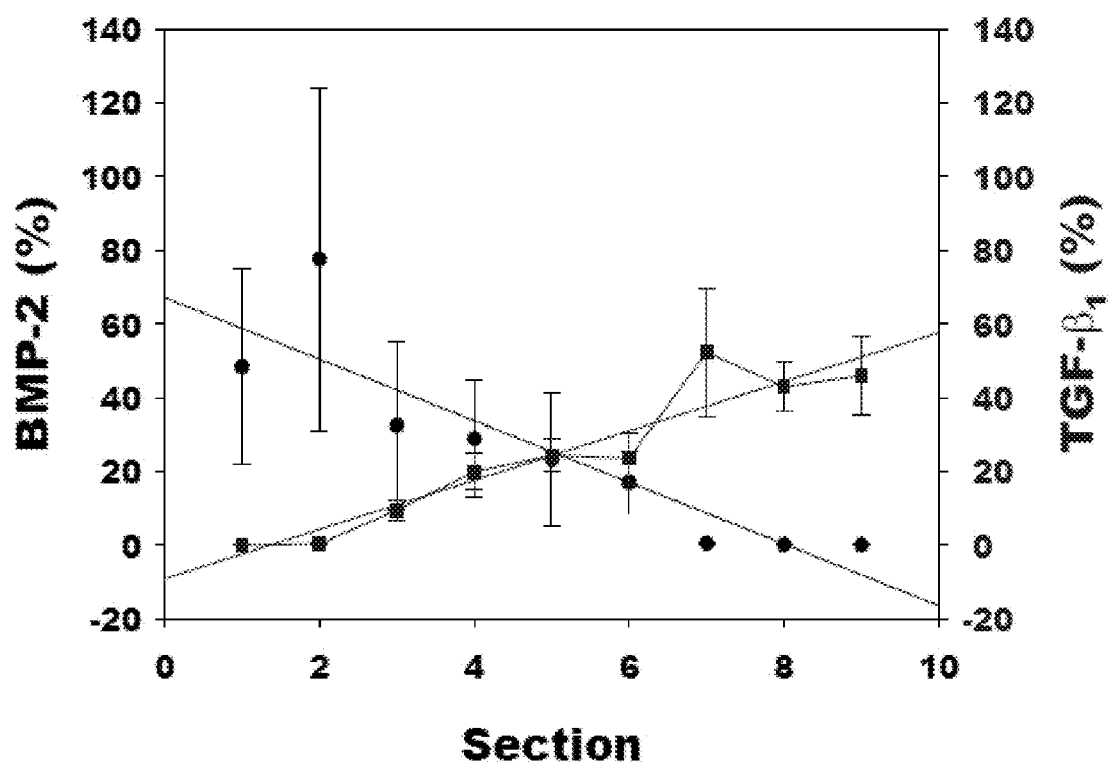
FIG. 7 is a plot showing quantification of BMP-2 and TGF-$\beta_1$ gradients in alginate hydrogel.

As noted above, the concentration gradients can be physically formed within the hydrogel to facilitate release of one or more bioactive agents according to a gradient release profile. The gradient release profile can refer to the amount and/or rate of release of a bioactive agent from the photocrosslinked degradable hydrogel. The gradient release profile can be selected for a particular hydrogel by modifying at least one property or characteristic (e.g., percentage of acrylation of natural polymers, concentration of attachment molecules, presence of carrier material, percentage of cross-links in hydrogel) of the material(s) (e.g., type of macromer(s) or carrier material) used to form the hydrogel. Depending upon the modified property or characteristic, a different gradient will be formed and a different release profile will be produced. During formation of the photocrosslinked biodegradable hydrogel, for example, the concentration of bioactive molecules incorporated into the hydrogel can be increased or decreased to increase or decrease the concentration gradient of the bioactive molecules upon release from the hydrogel. Examples of gradient release profiles for BMP-2 and TGF-$\beta_1$ from alginate hydrogel microbeads are illustrated in FIGS. 6 and 7. It will be appreciated that other techniques can be used to form hydrogels having at least one gradient, such as computer-controlled syringe pumps.

In another example of the present invention, the photocrosslinked biodegradable hydrogel can include at least one material or agent disposed on or within the hydrogel that is capable of carrying and differentially and/or controllably releasing at least one bioactive agent. For instance, the at least one agent or material can include a carrier material that is directly linked to the bioactive agent and/or physically associated with the bioactive agent. Carrier materials can include a variety of known microparticles or nanoparticles including, for example, polymer-based and calcium phosphate-based microparticles and nanoparticles. It will be appreciated that carrier materials may also have similar or identical material compositions as the photocrosslinked biodegradable hydrogel.

Polymer-based carrier materials can include a biodegradable polymer capable of controllably and/or differentially releasing at least one bioactive agent. For example, a polymer-based carrier material can be a biodegradable polymer in microparticle form. Microparticles can have a diameter less than 1 mm and typically between 1 and 200 microns. Microparticles can include both microspheres and microcapsules, and may have an approximately spherical geometry and be of fairly uniform size. Microspheres can have a homogeneous composition, and microcapsules can include a core composition (e.g., a bioactive agent) distinct from a surrounding shell. For the purposes of the present invention, the terms "microsphere," "microparticle," and "microcapsule" may be used interchangeably.

Microparticles can be made with a variety of biocompatible and biodegradable polymers. Examples of biocompatible, biodegradable polymers are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Other examples of materials that may be used to form microparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), collagen, fibrin, gelatin, glycosaminoglycans (GAG), poly(hyaluronic acid), poly(sodium alginate), alginate, hyaluronan, agarose, polyhydroxybutyrate (PHB), copolymers thereof, and blends thereof.

In one example of the present invention, a carrier material can comprise a microparticle made of poly(d,l-lactide-co-glycolide) (PLGA). PLGA degrades when exposed to physiological pH and hydrolyzes to form lactic acid and glycolic acid, which are normal byproducts of cellular metabolism. The disintegration rate of PLGA polymers may vary depending on the polymer molecular weight, ratio of lactide to glycolide monomers in the polymer chain, and stereoregularity of the monomer subunits. For example, mixtures of L and D stereoisomers that disrupt the polymer crystallinity can increase polymer disintegration rates. In addition, it will be appreciated that microspheres may contain blends of two or more biodegradable polymers of different molecular weight and/or monomer ratio.

Carrier materials can alternatively comprise a nanoparticle, such as submicron particles, for controlled release of the bioactive agent. A nanoparticle can have a diameter ranging from about less than 1 nanometer to about 1 micron. Nanoparticles can be created in the same manner as microparticles, except that high-speed mixing or homogenization may be used to reduce the size of the nanoparticle/bioactive agent emulsion(s) to less than about 2 microns. Alternative methods for nanoparticle production are known in the art and may be employed for the present invention.

In another example of the present invention, at least one bioactive agent can be incorporated on or within at least one calcium phosphate nanoparticle dispersed on or within the photocrosslinked biodegradable hydrogel. The at least one calcium phosphate nanoparticle can differentially or controllably release the at least one bioactive agent or be taken up (e.g., via endocytosis) by at least one cell to modulate the function and/or characteristic of the cell. The at least one bioactive agent may be at least partially coated on the surface of at least one calcium phosphate nanoparticle. Alternatively, the at least one bioactive agent may be dispersed, incorporated, and/or impregnated within the calcium phosphate nanoparticle. For example, a bioactive agent comprising a DNA plasmid (e.g., a plasmid encoding BMP-2) can be coated onto the surface of the calcium phosphate nanoparticle. Alternatively, a DNA plasmid can be co-precipitated with calcium phosphate to form the calcium phosphate nanoparticle. After forming the calcium phosphate nanoparticles, the nanoparticles can be coated with DNA or protein to prevent nanoparticle aggregation and/or promote cellular uptake. It will be appreciated that one or more of the same or different bioactive agents can be incorporated on or within the at least one calcium phosphate nanoparticle.

Calcium phosphate nanoparticles can have an average particle size of between about 1 nm and about 200 nm. It will be appreciated that smaller or larger calcium phosphate nanoparticles may be used. The calcium phosphate nanoparticles can have a generally spherical morphology and be of a substantially uniform size or, alternatively, may be irregular in morphology. Calcium phosphate nanoparticles may be complexed with surface modifying agents to provide a threshold surface energy sufficient to bind material (e.g., bioactive agents) to the surface of the nanoparticle without denaturing the material. Non-limiting examples of surface modifying agents can include basic or modified sugars, such as cellobiose, carbohydrates, carbohydrate derivatives, macromolecules with carbohydrate-like components characterized by an abundance of —OH side groups and polyethylene glycol.

In another example of the present invention, a bioactive agent can comprise an interfering RNA molecule incorporated on or within at least one carrier material dispersed on or within the photocrosslinked biodegradable hydrogel. The interfering RNA molecule can include any RNA molecule that is capable of silencing a target mRNA and thereby reducing or inhibiting expression of a polypeptide encoded by the target mRNA. Alternatively, the interfering RNA molecule can include a DNA molecule encoding for a shRNA of interest. For example, the interfering RNA molecule can comprise a short interfering RNA (siRNA) or microRNA molecule capable of silencing a target mRNA that encodes any one or combination of the polypeptides or proteins described above. The at least one carrier material can differentially or controllably release the at least one interfering RNA molecule or be taken up (e.g., via endocytosis) by at least one cell to modulate a function and/or characteristic of the cell.

In another aspect of the present invention, the photocrosslinked biodegradable hydrogel can include first and second bioactive agents disposed on or within the hydrogel. The first and second bioactive agents may comprise the same or different agents. As described in further detail below, the first and second bioactive agents can be differentially, sequentially, and/or controllably released from the photocrosslinked biodegradable hydrogel to modulate a different function and/or characteristic of a cell. It will be appreciated that the first bioactive agent can have a release profile that is the same or different from the release profile of the second bioactive agent from the photocrosslinked biodegradable hydrogel. The first and second bioactive agents may be dispersed uniformly on or within the photocrosslinked biodegradable hydrogel or, alternatively, dispersed such that different densities of the bioactive agents are localized on or within different portions of the hydrogel. It should also be appreciated that the macromer scaffold can be in either a hydrated or lyophilized state prior to the addition of bioactive agents. For example, the macromer scaffold can be in a lyophilized state before the addition of bioactive agents is done to re-hydrate and populate the scaffold with bioactive agents.

Alternatively, at least one bioactive agent can be chemically modified to include a moiety that can be used to couple the at least one bioactive agent to the macromer. For example, at least one bioactive agent can be acrylated (e.g., methacrylated). The acrylated bioactive agent can be cross-linked with the acrylate macromer to form a cross-linked biodegradable hydrogel. The acrylated bioactive agent can also be cross-linked with acrylated heparin and acrylated alginate to vary the mechanical properties of the hydrogel.

In another aspect of the present invention, the photocrosslinked biodegradable hydrogel can include first and second bioactive agents respectively incorporated on or within first and second carrier materials. The first and second carrier materials may comprise the same or different materials. Additionally, the first and second bioactive agents may comprise the same or different agents. As described in further detail below, the first and second carrier materials can differentially, sequentially, and/or controllably release the first and second bioactive agents to modulate a different function and/or characteristic of a cell. It will be appreciated that the first carrier material can release the first bioactive agent with a different release profile than the release profile of the second bioactive agent from the second carrier material. Additionally, it will be appreciated that the first carrier material can degrade or diffuse before the degradation or diffusion of the second carrier material or allow for an increased rate of release or diffusion of the first bioactive agent compared to the release of the second bioactive agent. The first and second carrier materials may be dispersed uniformly on or within the photocrosslinked biodegradable hydrogel or, alternatively, dispersed such that different densities of carrier materials are localized on or within different portions of the hydrogel.

Another aspect of the invention relates to a method of forming a photocrosslinked biodegradable hydrogel that is capable of serving as a substrate for the incorporation and/or attachment of at least one bioactive agent and at least one cell. The method can include reacting at least one acryl group with at least one natural polymer macromer to form a mixture comprising a plurality of acrylated macromers. The mixture can be contacted or combined with a photoinitiator that can initiate cross-linking of the macromers. The mixture can be exposed to a light source to initiate cross-linking of the macromers and thereby form a plurality of natural polymer macromers cross-linked with a plurality of hydrolyzable acrylate cross-links.

FIG. 1 illustrates an example of a method of forming a photocrosslinked biodegradable hydrogel comprising a plurality of methacrylated alginate macromers cross-linked with a plurality of hydrolyzable methacrylate cross-links. The method includes preparing methacrylated alginate macromers by reacting low molecular weight alginate with 2-aminoethyl methacrylated (AEMA). Low molecular weight sodium alginate can be prepared by irradiating the alginate at a gamma dose of about 5 Mrad/hr for about 4 hours. The low molecular weight sodium alginate can then be dissolved in a buffer solution (about 1 w/v % at a pH of about 6.5) of about 50 mM 2-morpholinoethanesulfonic acid (MES) containing about 0.5 M NaCl. N-hydroxysuccinimide (NHS) and 1-ethyl-3-(3-dimethylaminopropyl)-carbodiimide hydrochloride (EDC) (at an NHS:EDC ratio of about 1:2) can be added to the solution to activate the carboxylic acid groups of the alginate. After about 5 minutes, AEMA can be added to the solution. The reaction can be maintained at room temperature for about 24 hours. After the reaction, the mixture can be precipitated by pouring into an excess of acetone, drying under reduced pressure, and rehydrating to about a 1% w/v solution in ultrapure deionized water (diH$_2$O) for further purification. The methacrylated alginate can be purified by dialysis in diH$_2$O using a dialysis membrane for 3 days, followed by filtering through about a 0.22 µm filter, and then lyophilization.

The methacrylated alginate can then be modified with at least one attachment molecule. For example, at least one attachment molecule having the amino acid sequence of SEQ ID NO: 1 can be reacted with the methacrylated alginate about 5 minutes after forming the methacrylated alginate. The reaction mixture can then be maintained at room temperature for about 24 hours. Next, the modified alginate can be purified with dialysis in diH$_2$O for about 3 days. After dialysis, about 0.5 g of activated carbon can be added for about every 1 g alginate. The solution can then be lyophilized after removing the activated carbon by filtration.

After forming the methacrylated alginate, either with or without attachment molecules, the methacrylated alginate can be photocrosslinked by dissolving a desired amount of the alginate in an appropriate amount of diH$_2$O or aqueous media (e.g., PBS). A desired amount of a photoinitiator (e.g., Irgacure D2959) can then be added to the solution. The solution can then be injected into a curing vessel (e.g., two glass plates separated by spacers) and exposed to a light source at a wavelength and for a time to promote cross-linking of the methacrylated alginate macromers and form the photocrosslinked biodegradable hydrogel. For example, the methacrylated alginate can be exposed to UV light of about 365 nm at about 8 to 20 mW/cm$^2$ for about 8 minutes to form the hydrogel.

Figure 8:
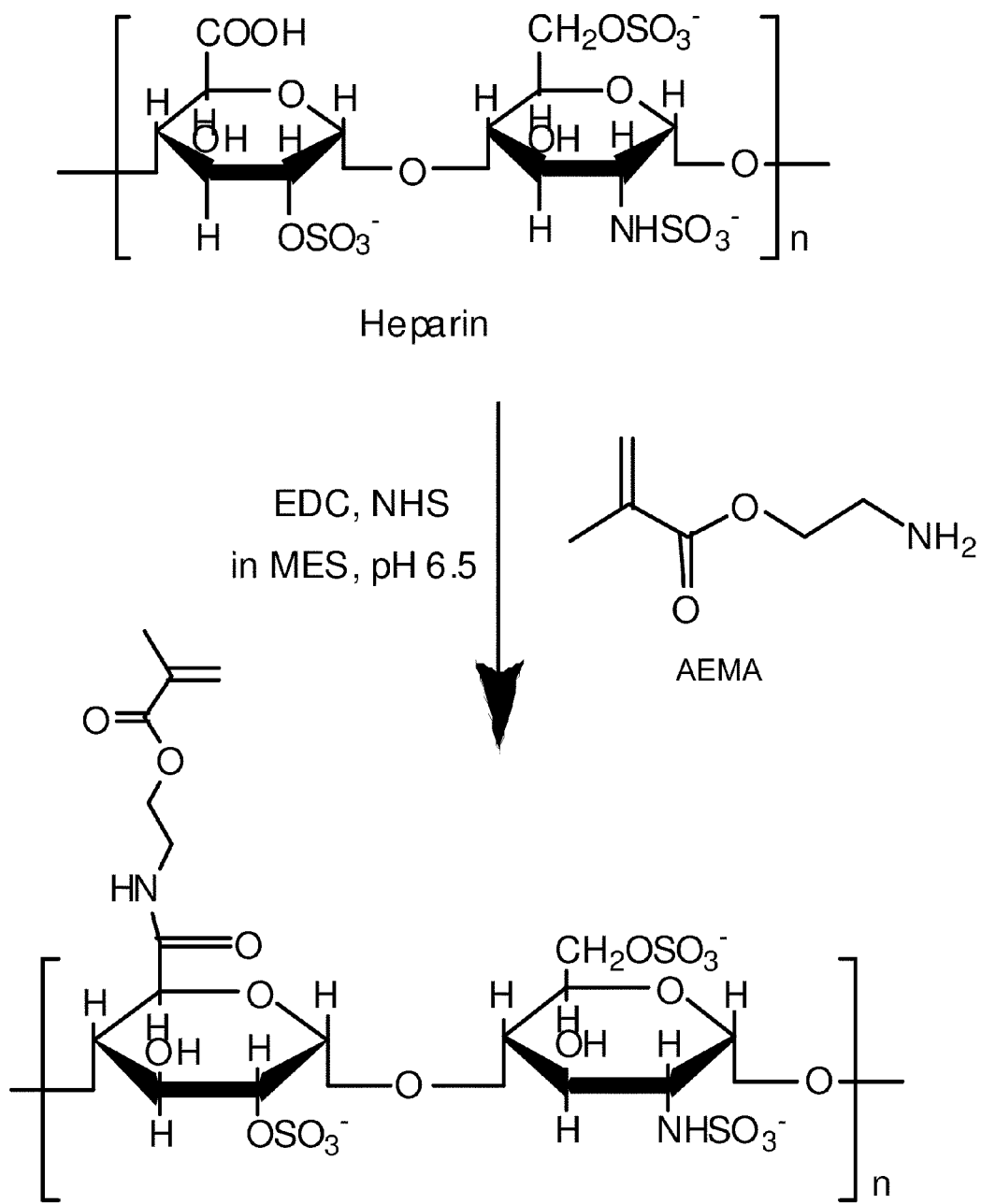
FIG. 8 a schematic illustration showing a process for preparing a methacrylated heparin macromer.

In another example of the present invention, the method can include forming a heparin-modified, photocrosslinked biodegradable hydrogel. As shown in FIG. 8, the method can include immersing heparin in MES. The heparin can be dissolved in a buffer solution (about 10 w/v % at about pH 6.5) of about 50 mM MES containing about 0.5 M NaCl. NHS and EDC (at an NHS:EDC ratio of about 1:2) can be added to the solution to activate the carboxylic acid groups of heparin. After about 5 minutes, AEMA can be added to the solution. The reaction may be maintained at about room temperature for about 24 hours. After the reaction, the mixture can be precipitated by pouring into an excess of acetone, drying under a vacuum, and rehydrating to about a 10% w/v solution in $diH_2O$ for further purification. Methacrylated alginate can then be purified by dialysis in $diH_2O$ using a dialysis membrane for about 3 days, filtered through about a 0.22 μm filter, and the lyophilized until dry. It will be appreciated that heparin can be used in varying concentration to control the release rate of a bioactive agent or agents.

After forming the heparin-modified, methacrylated alginate macromers, either with or without attachment molecules, the macromers can be photocrosslinked by dissolving a desired amount of the macromers in an appropriate amount of $diH_2O$. A desired amount of a photoinitiator (e.g., Irgacure D2959) can then be added to the solution. The solution can then be injected into a curing vessel (e.g., two glass plates separated by spacers) and exposed to a light source at a wavelength and for a time to promote cross-linking of the heparin-modified methacrylated alginate macromers and form the photocrosslinked biodegradable hydrogel. For example, the heparin-modified methacrylated alginate macromers can be exposed to UV light of about 365 nm at about 8 to 20 $mW/cm^2$ for about 8 minutes to form the hydrogel.

Figure 9:
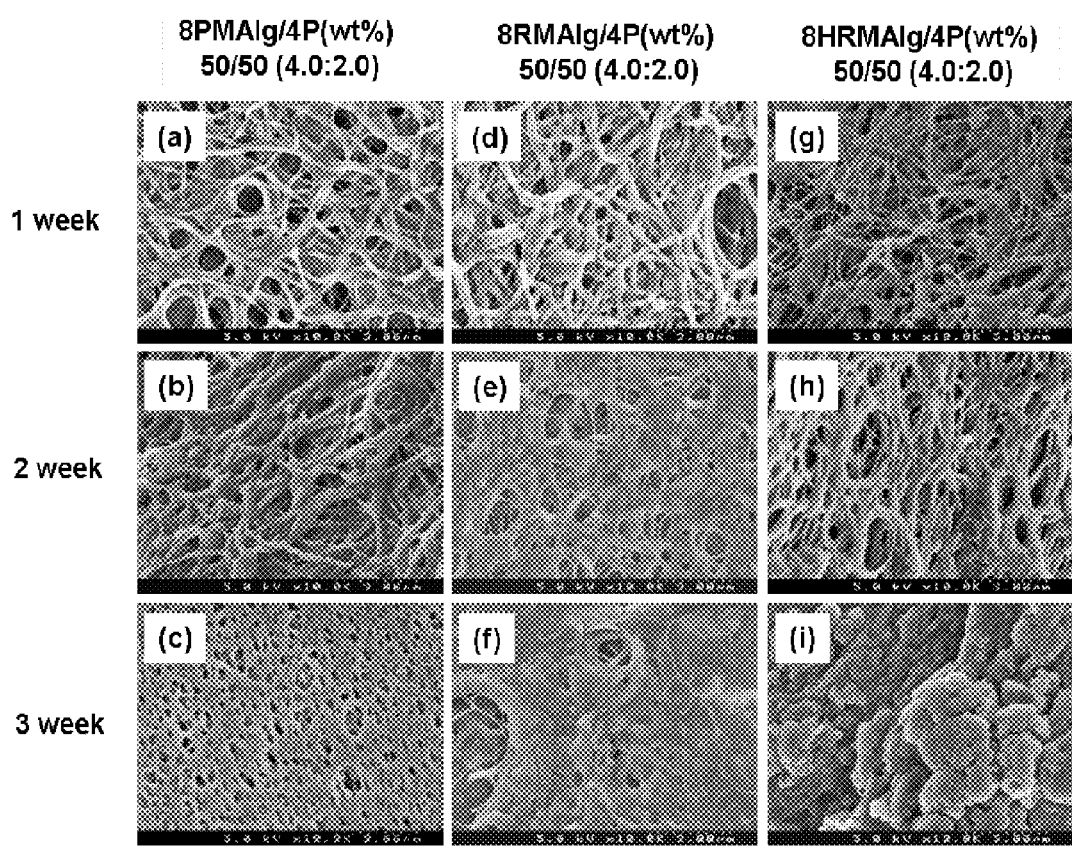
FIG. 9 is a series of scanning electron micrographs of polyethylene oxide (PEO) extracted electrospun pure-, RGD-, and heparin-RGD-modified methacrylated alginate nanofiber in $dH_2O$ at 37° C. for 3 weeks (images represent (a) 8PMAlg/4PEO, (b) 8RMAlg/4PEO, and (c) 8HRMAlg/4PEO)

It will be appreciated that the method can include the additional step of electrospinning acrylated monomers with or without a carrier material (e.g., polyethylene oxide or PEO) (FIG. 9). For example, Table 1 illustrates electrospinning conditions of photocrosslinked alginate/PEO nanofibrous scaffolds.

Generally, cells can be introduced into the photocrosslinked biodegradable hydrogel in vitro, although in vivo seeding approaches can optionally or additionally be employed. Cells may be mixed with the photocrosslinked biodegradable hydrogel and cultured in an adequate growth (or storage) medium to ensure cell viability. If the photocrosslinked biodegradable hydrogel is to be implanted for use in vivo after in vitro seeding, for example, sufficient growth medium may be supplied to ensure cell viability during in vitro culture prior to in vivo application. Once the photocrosslinked biodegradable hydrogel has been implanted, the nutritional requirements of the cells can be met by the circulating fluids of the host subject.

Any available method may be employed to introduce the cells into the photocrosslinked biodegradable hydrogel. For example, cells may be injected into the photocrosslinked biodegradable hydrogel (e.g., in combination with growth medium) or may be introduced by other means, such as pressure, vacuum, osmosis, or manual mixing. Alternatively or additionally, cells may be layered on the photocrosslinked biodegradable hydrogel, or the hydrogel may be dipped into a cell suspension and allowed to remain there under conditions and for a time sufficient for the cells to incorporate within or attach to the hydrogel. Generally, it is desirable to avoid excessive manual manipulation of the cells in order to minimize cell death during the impregnation procedure. For example, in some situations it may not be desirable to manually mix or knead the cells with the photocrosslinked biodegradable hydrogel; however, such an approach may be useful in those cases in which a sufficient number of cells will survive the procedure. Cells can also be introduced into the photocrosslinked biodegradable hydrogel in vivo simply by placing the hydrogel in the subject adjacent a source of desired cells. Bioactive agents released from the photocrosslinked biodegradable hydrogel may also recruit local cells, cells in the circulation, or cells at a distance from the implantation or injection site.

TABLE 1

Electrospinning Conditions of Photocrosslinked Alginate/PEO Nanofibrous Scaffolds

| | | | | Electrospinning conditions | | | |
| --- | --- | --- | --- | --- | --- | --- | --- |
| Sample code | MA-pure- And RGD-alginate[a] Concentration (wt %) | PEO Concentration[a] (wt %) (Mv = 900,000) | Alginate:PEO (vol/vol %) | Voltage (kV) | Needle size (G) | Tip-to-collector distance (cm) | Flow rate (ml/min) |
| 1PMAlg/4PEO | 1.0 | 4.0 | 50:50 (0.5:2.0) | 9.4-10.4 | 20 | 15 | 0.2 0.05 |
| 2PMAlg/4PEO | 2.0 | | 50:50 (1.0:2.0) | | | | |
| 4PMAlg/4PEO | 4.0 | | 50:50 (2.0:2.0) | | | | |
| 8PMAlg/4PEO | 8.0 | | 50:50 (4.0:2.0) | | | | |
| 8RMAlg/4PEO | 8.0 | 4.0 | 50:50 (4.0:2.0) | | | | |
| 8HRMAlg/4PEO | 8.0 | 4.0 | 50:50 (4.0:2.0) | | | | |

[a]Methacrylated alginate and PEO were dissolved in $diH_2O$ (10 ml) with 0.05 w/v photoinitiator.

It should also be appreciated that the photocrosslinked biodegradable hydrogel can be formed with at least one cell and/or bioactive agent. For example, a plurality of cells may be dispersed in a substantially uniform manner on or within the hydrogel or, alternatively, dispersed such that different densities and/or spatial distributions of different or the same cells are dispersed within different portions of the hydrogel. The cells can be autologous, allogeneic or xenogeneic. It will also be appreciated that the cells may be seeded before or after the macromers are photocrosslinked. Alternatively, photocrosslinked hydrogels can be incubated in a solution of at least one bioactive agent after the macromers are crosslinked.

As those of ordinary skill in the art will appreciate, the number of cells to be introduced into the photocrosslinked biodegradable hydrogel will vary based on the intended application of the hydrogel and on the type of cell used. Where dividing autologous cells are being introduced by injection or mixing into the photocrosslinked biodegradable hydrogel, for example, a lower number of cells can be used. Alternatively, where non-dividing cells are being introduced by injection or mixing into the photocrosslinked biodegradable hydrogel, a larger number of cells may be required. It should also be appreciated that the macromer scaffold can be in either a hydrated or lyophilized state prior to the addition of cells. For example, the macromer scaffold can be in a lyophilized state before the addition of cells is done to re-hydrate and populate the scaffold with cells.

In an example of the present invention, a plurality of chondrocytes can be seeded on onto the photocrosslinked biodegradable hydrogel at a desired density and allowed to adhere thereto for a period of time. The chondrocytes can be obtained from a host subject and then expanded ex vivo to a desired density. For example, about $1 \times 10^4$ cells/cm$^2$ can be seeded onto a photocrosslinked biodegradable hydrogel and then allowed to adhere thereto for about 4 hours. Alternatively, at least one cell can be partly or entirely encapsulated in the photocrosslinked biodegradable hydrogel. To encapsulate at least one chondrocyte, for example, a population of chondrocytes can be suspended a methacrylated alginate solution (about 2 w/v % in DMEM) with about 0.05 w/v % photoinitiator. The cell/macromer solutions (about 300 µl) can then be pipetted into a vessel (e.g., a 96-well culture plate) at a desired density (e.g., $1 \times 10^7$ cells/ml) and photocrosslinked with UV for about 10 minutes. The resulting cell-seeded hydrogel can be placed in culture or used for a desired tissue engineering application, for example.

To form a photocrosslinked biodegradable hydrogel with at least one bioactive agent, a methacrylated alginate solution can be completely dissolved in diH$_2$O or other aqueous media and then mixed with a desired amount of a photoinitiator. At least one growth factor (e.g., TGF-β1, bFGF, VEGF or BMP-2) can then be added to the solution at a desired concentration (e.g., about 0.5 µg/ml). Aliquots of the solution can then be placed in a container (e.g., a 96-well plate) and photocrosslinked with about 365 nm UV light at about 8 to 20 mW/cm$^2$ for about 8 minutes.

The photocrosslinked biodegradable hydrogel can be used in a variety of biomedical applications, including tissue engineering, drug discovery applications, and regenerative medicine. In one example of the present invention, a photocrosslinked biodegradable hydrogel can be used to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the photocrosslinked biodegradable hydrogel can be administered to the target site. The hydrogel can be prepared according to the method described above. For example, a plurality of cells, such as chondrocytes may be mixed with a plurality of methacrylated alginate macromers to form a solution. The solution may also be mixed with at least one attachment molecule, such as a an acrylated or methacrylated polypeptide having the amino acid sequence of SEQ ID NO: 1. For example, this step can be carried out if the at least one attachment molecule is mixed with an acrylated or methacrylated solution prior to crosslinking. Otherwise, the at least one attachment molecule can be previously bound to the alginate macromers using carbodiimide chemistry, for example. Chondrocytes may be obtained from a host subject and then expanded to a desired density ex vivo.

Next, the biodegradable hydrogel may be loaded into a syringe or other similar device and injected or implanted into the tissue defect. Upon injection or implantation into the tissue defect, the biodegradable hydrogel be formed into the shape of the tissue defect using tactile means. Alternatively, the biodegradable may be formed into a specific shape prior to injection or implantation into the subject. A transdermal light source (e.g., a UV light source) can then be applied to the area of the subject's skin substantially adjacent the tissue defect to promote photocrosslinking of the methacrylated alginate macromers and formation of a photocrosslinked biodegradable hydrogel having substantially identical dimensions of the tissue defect. Alternatively, it will be appreciated that the light source can be directly applied to the hydrogel where the hydrogel is first placed in an open wound or defect.

After implanting the photocrosslinked biodegradable hydrogel into the subject, the chondrocytes can begin to migrate from the hydrogel into the tissue defect, express growth and/or differentiation factors, and/or promote chondroprogenitor cell expansion and differentiation. Additionally, the presence of the photocrosslinked biodegradable hydrogel in the tissue defect may promote migration of endogenous cells surrounding the tissue defect into the photocrosslinked biodegradable hydrogel. Once implanted, the amide and/or ester linkages of the hydrolyzable methacrylated cross-links can be hydrolyzed. Hydrolysis of the methacrylated cross-links can occur at a controlled rate and lead to controlled degradation of the photocrosslinked biodegradable hydrogel. This hydrolytic degradation can create space for cell growth and deposition of a new extracellular matrix to replace the hydrogel.

In another example of the present invention, a photocrosslinked biodegradable hydrogel can be prepared according to the method described above. For example, a photocrosslinked biodegradable hydrogel can comprise: a plurality of polypeptide-modified, methacrylated alginate macromers cross-linked with a plurality of hydrolyzable methacrylate cross-links; at least one CD34$^+$ MSC; and first and second carrier materials respectively including first and second bioactive agents. The methacrylated alginate macromers can be modified with at least one polypeptide having the amino acid sequence of SEQ ID NO: 1. Each of the first and second carrier materials can be comprised of PLGA and may be prepared as described above. For example, the first carrier material may comprise a greater mixture of L and D stereoisomers to increase the degradation rate of the first carrier material. Additionally, the second carrier material may comprise a lower mixture of L and D stereoisomers (as compared to the first carrier material) so that the second carrier material has a slower degradation rate when exposed to physiological conditions.

The first and second bioactive agents may then be impregnated into and/or coated onto the first and second carrier materials, respectively. The first bioactive agent can comprise a growth factor (e.g., TGF-β, VEGF and/or FGF-2) or, alternatively, a plasmid including a polynucleotide that encodes a growth factor (e.g., TGF-β, VEGF and/or FGF-2). Similarly, the second bioactive agent can comprise a growth factor (e.g., IGF-I and/or BMP-2) or, alternatively, a plasmid including a polynucleotide that encodes a growth factor (e.g., IGF-I and/or BMP-2). It should be appreciated that in order to regenerate bone, FGF-2 and/or VEGF can be incorporated into the first bioactive agent and BMP-2 (or a DNA plasmid encoding BMP-2) can be incorporated into first and second carrier materials (e.g., made of PLGA).

Next, at least one CD34$^+$ MSC may be obtained from a source (e.g., the bone marrow of the host subject) and then expanded ex vivo (e.g., using FGF-2) to a desired density. After expanding the cells to a desired density, the cells can be mixed with the methacrylated alginate macromers to form a mixture. The biodegradable hydrogel may then be loaded into a syringe or other similar device and injected or implanted into the tissue defect. A transdermal light source (e.g., a UV light source) can then be applied to the area of the subject's skin substantially adjacent the tissue defect to promote photocrosslinking of the methacrylated alginate macromers and formation of a photocrosslinked biodegradable hydrogel having substantially identical dimensions of the tissue defect. Alternatively, it will be appreciated that the light source can be directly applied to the hydrogel where the hydrogel is first placed in an open wound or defect.

After implanting the photocrosslinked biodegradable hydrogel in the subject, the first carrier material may begin to degrade faster than the second carrier material (or allow for increased diffusion relative to the first carrier material) and thereby release the growth factor (e.g., TGF-β) or the polynucleotide encoding the growth factor. Release of TGF-β from the first carrier material can promote early CD34$^+$ MSC commitment to a particular lineage (e.g., chondrogenic lineage). As the cells proliferate, the second carrier material may degrade more slowly than the first carrier material and thereby release the other growth factor (e.g., IGF-I) or the polynucleotide encoding the other growth factor at a slower rate. Release of IGF-I from the second carrier material can promote differentiation of the cells into more mature cells (e.g., chondroprogenitor cells). The continued release of IGF-I, along with other growth and/or differentiation factors expressed by the cells (i.e., the cells comprising the hydrogel as well as the cells surrounding the tissue defect), can promote development of mature cells (e.g., chondrocytes) capable of generating new tissue (e.g., cartilage) for repair of the tissue defect. Additionally, the amide and/or ester linkages of the hydrolyzable methacrylated cross-links can be hydrolyzed upon implantation of the photocrosslinked biodegradable hydrogel. Hydrolysis of the methacrylated cross-links can occur at a controlled rate and lead to controlled degradation of the photocrosslinked biodegradable hydrogel. This hydrolytic degradation can create space for cell growth and deposition of a new extracellular matrix to replace the photocrosslinked biodegradable hydrogel.

In another example of the present invention, a method is provided for forming a high density cell aggregate. The high density cell aggregate can comprise a population of cells, a plurality of photocrosslinked biodegradable hydrogels, and at least one bioactive agent incorporated on or within the hydrogels. The photocrosslinked biodegradable hydrogels can be formed into nanoparticles and/or microparticle, and the cells can include undifferentiated progenitor cells, substantially differentiated progenitor cells, and/or differentiated cells.

One step of the method can include forming a plurality of photocrosslinked biodegradable hydrogels into nanoparticles and/or microparticles. The hydrogels can be formed as described above, for example, and include a plurality of cross-linked methacrylated alginate macromers. After forming the plurality of photocrosslinked biodegradable hydrogels, the hydrogels can be loaded with at least one bioactive agent. Methods for forming nanoparticles and/or microparticles loaded with bioactive agents are known in the art.

After loading the photocrosslinked biodegradable hydrogels, the hydrogels can be mixed with a population of cells to form a cell aggregate. The cells can include any totipotent stem cell, pluripotent stem cell, or multipotent stem cell, and/or differentiated cell. Progenitor cells can include autologous cells; however, it will be appreciated that xenogeneic, allogeneic, or syngeneic cells may also be used. The progenitor cells employed may be primary cells, expanded cells or cell lines, and may be dividing or non-dividing cells. The cells can be derived from any desired source. For example, the cells may be derived from primary tissue explants and preparations thereof, cell lines (including transformed cells) that have been passaged once (P1), twice (P2), or even more times, or host cells (e.g., human hosts). Any known method may be employed to harvest cells for use in the present invention. For example, MSCs, which can differentiate into a variety of mesenchymal or connective tissues (e.g., adipose tissue, osseous tissue, cartilaginous tissue, elastic tissue, and fibrous connective tissues), can be isolated according to the techniques disclosed in U.S. Pat. No. 5,486,359 to Caplan et al. and U.S. Pat. No. 5,226,914 to Caplan et al., the entireties of which are hereby incorporated by reference. In one example of the present invention, the population of cells can comprise a population of human CD 34$^+$ MSCs.

Once the cells and the photocrosslinked biodegradable hydrogels have been mixed, the cell aggregate can be centrifuged at a desired acceleration and for a desired period of time to form the high density cell aggregate. The photocrosslinked biodegradable hydrogels may be dispersed throughout the aggregate in a substantially uniform manner. The bioactive agent can then be released from the photocrosslinked biodegradable hydrogels via diffusion and/or as the hydrogels begin to degrade. Controlled release of the bioactive agent from the particles may be dependent on the size and composition of the photocrosslinked biodegradable hydrogels, as well as the composition of the medium in which the aggregate is immersed. For example, the release rate of the bioactive agent(s) can be selectively controlled by changing the degree or percent of macromer methacrylation and/or the macromer concentration.

The high density cell aggregate can allow for substantially more uniform spatial delivery of the bioactive agent throughout the interior of the aggregate. The substantially uniform distribution of the photocrosslinked biodegradable hydrogels and relatively uniform release of the bioactive agent in the high density cell aggregate is advantageous for several reasons, including, but not limited to: (1) rapidly inducing uniform cell differentiation; (2) reducing or eliminating in vitro culture of aggregates prior to utilization in in vivo regeneration strategies; (3) providing control over the temporal presentation of growth factors; and (4) allowing for the use of lower concentrations of growth factors as compared to systems employing exogenously-supplied growth factors.

It will be appreciated that the high density cell aggregate can further include additional photocrosslinked biodegradable hydrogels that include second bioactive agents. The second bioactive agents may be the same or different type of agent (described above). The photocrosslinked biodegradable hydrogels can differentially, sequentially, and/or controllably release the different bioactive agents to modulate the same or different function and/or characteristics of at least one cell in the aggregate. The bioactive agents can have the same or different release profiles from the photocrosslinked biodegradable hydrogels.

The following example is for the purpose of illustration only and is not intended to limit the scope of the claims, which are appended hereto.

Example 1

Synthesis of Methacrylated Alginate

The methacrylated alginate was prepared by reacting low molecular weight alginate with 2-aminoethyl methacrylate (AEMA, Sigma, St. Louis, Mo., USA). Low molecular weight of sodium alginate was prepared by irradiating Protanal LF 20/40 (FMC Biopolymer, Philadelphia, Pa., USA) at a gamma dose of 5 Mrad/hr for 4 hours. Low molecular weight sodium alginate was dissolved in a buffer solution (1 w/v %, pH 6.5) of 50 mM 2-morpholinoethanesulfonic acid (MES, Sigma) containing 0.5 M NaCl. N-hydroxysuccinimide (NHS, Sigma) and 1-ethyl-3-(3-dimethylaminopropyl)-carbodiimide hydrochloride (EDC, Sigma) (NHS:EDC=1:2) were added to the solution to activate the carboxylic acid groups of the alginate. After 5 min, AEMA was added to the solution. The reaction was maintained at room temperature for 24 hours. After the reaction, the mixture was precipitated by pouring into an excess of acetone, dried under reduced pressure, and rehydrated to a 1% w/v solution in ultrapure deionized water ($diH_2O$) for further purification. The methacrylated alginate was purified by dialysis in $diH_2O$ using dialysis membrane (MWCO 3500; Spectrum Laboratories Inc., Rancho Dominguez, Calif., USA) for 3 days, filtered through a 0.22 µm filter, and lyophilized.

Photocrosslinking

To fabricate photocrosslinkable alginate hydrogel, methacrylated alginate (0.2 g) was dissolved in $diH_2O$ (10 ml) with 0.05 w/v % photoinitiator (Irgacure D-2959, Sigma). The alginate solution was injected between two glass plates separated by 0.75 mm spacers and photocrosslinked with 365 nm UV light at ~8-20 mW/cm$^2$ for 8 min to form the hydrogel. Photocrosslinked hydrogel disks were punched out using a 6 mm diameter biopsy punch and placed in the $diH_2O$.

$^1$H-NMR Characterization

Methacrylated alginate was dissolved in deuterium oxide with 0.05 w/v % photoinitiator, placed in NMR tube, and photocrosslinked at 365 nm UV light at ~8-20 mW/cm$^2$ for 8 min to form a hydrogel. The $^1$H-NMR spectra of the photocrosslinked alginate hydrogel were recorded using a Varian Unity-300 (300 MHz) NMR spectrometer (Varian Inc., Palo Alto, Calif., USA). To analyze the methacrylation efficiency of alginate, $^1$H-NMR spectra were also recorded for uncrosslinked, unmodified alginate and uncrosslinked, methacrylated alginate. The efficiency of alginate methacrylation was calculated from $^1$H-NMR spectra based on the ratio of the integrals for the alginate protons and the methylene protons of methacrylate.

Swelling and In Vitro Degradation of Photocrosslinked Alginate Hydrogel

The photocrosslinked alginate hydrogels were lyophilized until dry and dry weights ($W_d$) were measured. Dried hydrogel samples (n=3) were immersed in 50 ml of $diH_2O$ at 37° C. and allowed to swell. Swollen hydrogel samples were weighted as $W_s$ at different time points. The swelling ratio (Q) was calculated by $Q=W_s/W_d$.

The dried hydrogel samples (n=3) were weighed ($W_i$) and incubated in 50 ml of $diH_2O$ at 37° C. for in vitro degradation test. The $diH_2O$ was replaced every three days. At predetermined time points, the samples were removed, rinsed with $diH_2O$, lyophilized and weighed ($W_d$). The percent mass loss was calculated by $(W_i-W_d)/W_i \times 100$.

Mechanical Testing

The elastic moduli of the photocrosslinked alginate hydrogels was determined by performing constant strain rate compression tests using the Rheometrics Solid Analyzer (RSAII, Rheometrics Inc., Piscataway, N.J., USA). The photocrosslinked alginate hydrogel disks were prepared as described in section 2.2., and kept in $diH_2O$ at 37° C. At predetermined time points, swollen alginate hydrogel disks were punched once again 6 mm diameter disks, and uniaxial unconfined compression tests were performed on the swollen alginate hydrogels at room temperature using a constant crosshead speed of 1.0 cm/min and a load cell of 10N. Each compressive test was performed for less than 2 seconds to avoid loss of water during measurement. Compressive moduli of photocrosslinked alginate hydrogels were obtained from the slope of stress vs. strain curves, limited to the first 2% of strain.

The number average molecular weight between crosslinks ($M_c$) was calculated according to following equation; $M_c=3\rho RT/E$ (Jeon, O. et al., *Carbohyd Polym.* 70(3):251-257, 2007; Ravi, N. et al., *Polymer* 47(11):4203-4209, 2006). T is the temperature (298 K) at which the modulus was measured, ρ is the concentration of alginate (g/m$^3$) in the cross-linking solution, R is the gas constant (8.3145 Jmol$^{-1}$K$^{-1}$), and E is the compressive modulus.

Cytotoxicity of Methacrylated Alginate and Photocrosslinked Alginate Hydrogel

To evaluate cytotoxicities of methacrylated alginate and photocrosslinked alginate hydrogels, an indirect contact methodology was employed. Briefly, MC3T3-E1 Subclone 4 cells (ATCC CRL-2593, Manassas, Va., USA), a mouse preosteoblast cell line, were plated in 6-well plates at $1 \times 10^6$ cells/well in 3 ml of Dulbecco's modified eagle medium (DMEM) and cultured at 37° C., 95% humidity and 5% $CO_2$ for 24 h. Cell culture inserts (25 mm in diameter, 8 µm pore size on PET track-etched membrane; Becton Dickinson Labware Europe, Le Pont De Claix, France) were placed into each well. Sterile methacrylated alginate solution (1 ml, 2 w/v % in ultrapure deionized water) or a photocrosslinked alginate hydrogel (1 ml) was added into each culture insert (n=3). A control group, not exposed to any chemicals or inserts, was maintained in parallel. After 48 h incubation, media, inserts, and hydrogels were removed. Each well was rinsed with phosphate buffered saline (PBS), and 3 ml of a 20% CellTiter 96 Aqueous One Solution (Promega Corp., Madison, Wis., USA) in PBS was added into each well. The 3-[4,5-dimethylthiazol-2-yl]-5-[3-carboxymethoxy-phenyl]-2-[4-sulfophenyl]-2H-tetrazolium (MTS-tetrazolium) compound can be metabolized by mitochondria in living cells into a colored formazan product that is soluble in cell culture medium. After incubating at 37° C. for 90 min, the absorbance of the solutions was determined at 490 nm using a 96-well plate reader (SAFIRE, Tecan, Austria).

The viability of MC3T3 cells in the presence of methacrylated alginate and photocrosslinked alginate hydrogels was also investigated by a Live/Dead assay system (Sigma) comprised of fluorescein diacetate (FDA) and ethidium bromide (EB). FDA stains the cytoplasm of viable cells green, while EB stains the nuclei of non-viable cells orange-red. The staining solution was freshly prepared by mixing 1 ml of FDA solution (1.5 mg/ml of FDA in dimethyl sulfoxide and 0.5 ml of EB solution (1 mg/ml of EB in PBS) with 0.3 ml of PBS (pH 8). After 48 h incubation of the alginate with the cells, inserts and hydrogels were removed. Then, 60 μl of staining solution was added into each well and incubated for 3-5 min at room temperature. After staining, samples were examined on an inverted fluorescence microscope (ECLIPSE TE 300, Nikon, Tokyo, Japan) equipped with a digital camera (Retiga-SRV, QImaging, Burnaby, BC, Canada). Three images of each well were randomly selected for counting live and dead cells.

Viability Assay of Cells Photoencapsulated in Alginate Hydrogels

Chondrocytes isolated from bovine articular cartilage using a previously reported method (Hall, A. C. et al., *Am J Physiol.* 270 (5 Pt 1):C1300-1310, 1996) were photoencapsulated in alginate hydrogels by suspension in methacrylated alginate solution (2 w/v % in DMEM) with 0.05 w/v % photoinitiator (n=3). The cell/macromer solutions (500 μl) were pipetted into 24-well tissue culture plates ($1 \times 10^7$ cells/ml) and photocrosslinked with UV for 10 minutes. The resulting hydrogel-cell constructs were removed from the wells, placed in new 24-well tissue culture plates with 500 μl of fresh DMEM, and cultured in a humidified incubator at 37° C. with 5% $CO_2$ for 1 week. To determine the viability of the cells after encapsulation, MTS and Live/Dead assays were performed. After 1 week culture, the medium was discarded and the hydrogel-cell constructs were transferred into new wells after they were washed with PBS. 500 μl of a 20% CellTiter 96 Aqueous One Solution in PBS was added into each well. After incubating at 37° C. for 90 min, the hydrogel-cell constructs were homogenized and the absorbance of the solutions was determined at 490 nm using a 96-well plate reader. For the live/dead assay, 20 μl of staining solution was added into each well and incubated for 3-5 min at room temperature and then stained hydrogel-cell constructs were subjected to the fluorescence microscope.

Cell Culture on Photocrosslinked Alginate Hydrogels

MC3T3 cells were seeded on photocrosslinked alginate disks at a seeding density of $1 \times 10^4$ cells/$cm^2$ and allowed to adhere for 4 h. The photocrosslinked alginate disks were then transferred to new plates containing fresh media and cultured in an incubator. After 48 h incubation, alginate disks were removed from culture and stained using the FDA/EB to examine the viability and morphology of adhered cells.

Statistical Analysis

All quantitative data is expressed as mean±standard deviation. Statistical analysis was performed with one-way analysis of variance (ANOVA) with Tukey honestly significant difference post hoc test using Origin software (OriginLab Co., Northampton, Mass.). A value of $p<0.05$ was considered statistically significant.

Results

Synthesis and Characterization of Macromer and Photocrosslinked Hydrogel

To prepare the photocrosslinked biodegradable alginate hydrogel, methacryl groups were introduced into the alginate main chains as shown in FIG. 1. Alginate was covalently reacted with various amounts of AEMA. The theoretical methacrylation of carboxyl groups of alginate varied from 5% to 45%. Theoretical methacrylation was calculated on the basis of the concentration of AEMA added to the alginate solution (Table 2).

TABLE 2

Methacrylation efficiency (%) of alginates and mechanical properties of photocrosslinked alginate hydrogels with various degrees of methacrylated macromer

| Code | Theoretical methacrylation[a] (%) | Methacrylation efficiency[b] (%) | Elastic modulus[c] (kPa) | $M_c$ (g/mol) |
|---|---|---|---|---|
| MAALG-4 | 5.66 | 73 | —[d] | — |
| MAALG-8 | 11.31 | 67 | 34.92 ± 2.48 | 4257 |
| MAALG-14 | 22.63 | 61 | 133.57 ± 9.12 | 1113 |
| MAALG-25 | 45.26 | 56 | 170.70 ± 15.51 | 871 |

[a]Theoretical methacrylation was calculated by modification of total carboxylic acid in 2% (w/v) alginate solution and molecular weight of the repeat unit ($M_0$ = 198).
[b]Methacrylation efficiency was calculated from $^1$H-NMR data.
[c]Elastic modulus was measure after incubation in di$H_2$O at 37° C. for 24 hours.
[d]It was not possible to perform a compression test on the MAALG-4.

The experimental efficiency of alginate methacrylation was calculated from $^1$H-NMR spectra. The intensities of proton peaks of AMEA increased as the theoretical methacrylation of alginate increased from 5% to 45%.

The $^1$H-NMR spectra of methacrylated alginate showed that the peaks of vinyl methylene and methyl protons that were newly formed by the reaction with AEMA are located at 66.2 and 5.7, and 1.9, respectively. The completeness of photocrosslinking was also verified with $^1$H-NMR. After photocrosslinking of methacrylated alginate, the disappearance of the peaks of vinyl methylene and shift of methyl peak to δ1.2 in the $^1$H-NMR spectra indicate the complete reaction of the methacrylate group. The peak of newly formed methylene proton by the photocrosslinking appears at δ2.2.

Swelling Kinetics, Degradation, Mechanical Properties of Photocrosslinked Alginate Hydrogel The size of photocrosslinked alginate hydrogel slightly increased after one week. However, after two weeks, the size of alginate hydrogel had rapidly increased.

Figure 10:
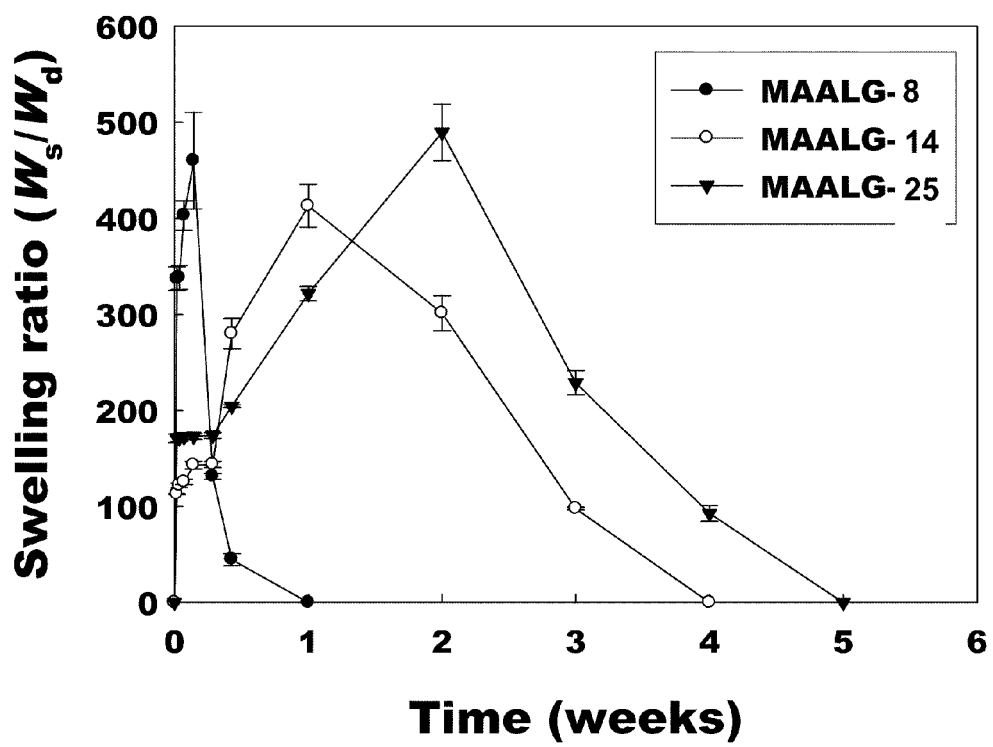
FIG. 10 illustrates the swelling ratios of photocrosslinked alginate hydrogels over time. Values represent mean and standard deviation (n=3)

Photocrosslinked alginate hydrogels were prepared with different methacrylation of alginate. The change of swelling ratio of the hydrogels over time was measured as this reflects changes in the physical and chemical structure of hydrogels. Swelling ratios of these hydrogels in di$H_2$O are shown in FIG. 10. All hydrogels exhibited fast swelling. The swelling of MAALG-14 and MAALG-25 reached equilibrium stage within 48 hrs, increased up to 1 and 2 weeks, respectively, and then gradually decreased. Compared to the MAALG-14 and MAALG-25, MAALG-8 exhibited much faster swelling kinetics. The swelling of MAALG-8 reached a maximum by 24 hrs and then rapidly decreased.

Figure 11:
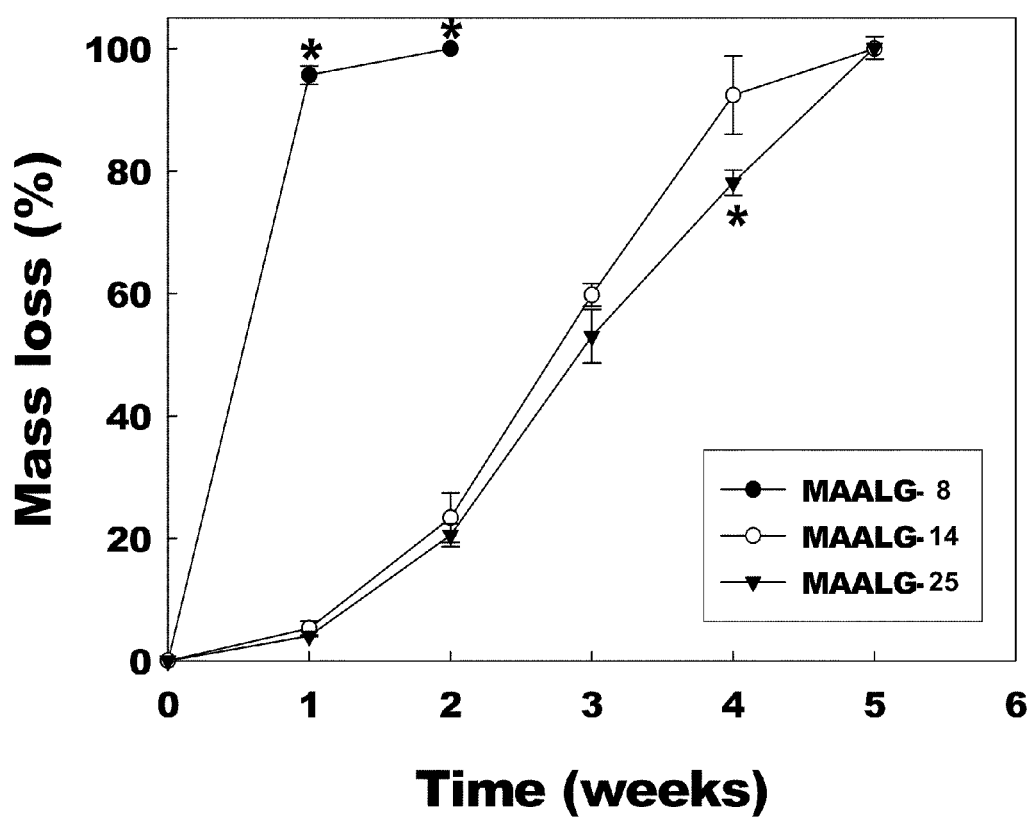
FIG. 11 is a plot comparing in vitro degradation of photocrosslinked alginate hydrogels over time. Mass loss (%)= $(W_i - W_d)/W_i \times 100$, where $W_i$=initial weight and $W_d$=weight after degradation. Values represent mean and standard deviation (n=3) (*p<0.05 with MAALG-14)

The mass loss (%) of alginate hydrogels over time was determined as a measure of degradation (FIG. 11). MAALG-8 displayed the fastest degradation with a mass loss of 95.67% at 1 week, while MAALG-25 showed the slowest degradation. As methacrylation of alginate increased from 14% to 25%, the degradation rate of the cross-linked hydrogels decreased (FIG. 11). However, photocrosslinked alginate hydrogels with methacrylation of 14% to 25% had relatively similar degradation rates, with complete degradation of both conditions occurring by 5 weeks.

To examine the correlation between mechanical property change and degradation, constant strain-rate compression tests were performed on the alginate hydrogels during the degradation study in order to determine their elastic moduli. Representative stress-strain curves of the MAALG-25 alginate hydrogels during the course of degradation are presented in FIG. 12A. It can be observed that the compressive stiffness of alginate hydrogels decreased with degradation time as supported by the elastic moduli results (FIG. 12B).

Cytotoxicity of Macromer and Photocrosslinked Alginate Hydrogel

The cytotoxicities of methacrylated alginate and photocrosslinked alginate hydrogel were evaluated by measuring the mitochondrial metabolic activity of MC3T3 cells in the presence of the biomaterial using a standard MTS assay. The cell viability was calculated by normalizing the absorbance of samples at 490 nm to that of the control without any macromer or insert in the medium. The viability of cells cultured in the presence of macromer and photocrosslinked MAALG-25 hydrogels (91% and 89%, respectively) was slightly lower than that of cells in the cells+insert group. There was no significant difference in cell viability after 48-hour culture between macromer and photocrosslinked alginate hydrogel.

Figure 13:
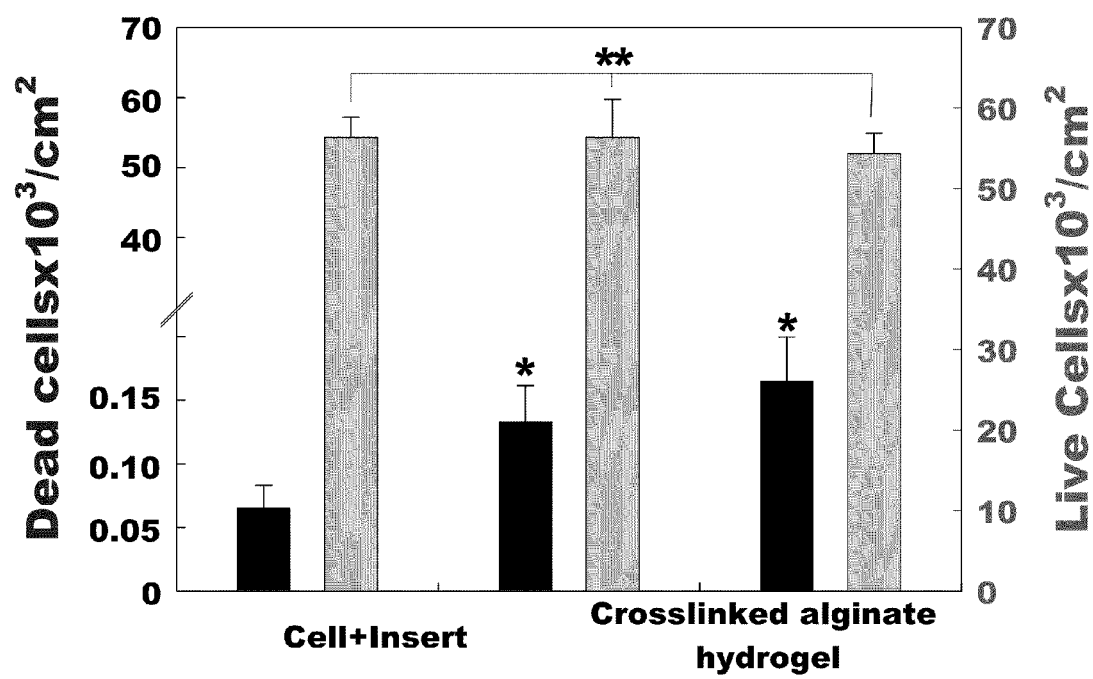
FIG. 13 is a graph showing the quantified cell density of live and dead cells for a cell culture insert, methacrylated alginate, or a photocrosslinked alginate hydrogel (cells were stained by FDA/EB. Green and orange-red colors indicate viable and dead cells, respectively. Values represent mean and standard deviation (N=3). The scale bar indicates 200 µm. *p<0.05, **p>0.05)

The cytotoxicity of photocrosslinked alginate hydrogel was also examined by fluorescence staining with a Live/Dead assay, where live cells and dead cells were fluorescently labeled green and red, respectively. Almost all of MC3T3 cells were live after 48 hr exposure to the alginate hydrogel. Quantification of stained images demonstrated that there was no significant difference in the number of live cells between the control cells+insert group and the alginate hydrogel group (FIG. 13). Although the number of dead cells in the hydrogel exposed group was larger than that of cells+insert group, the number of dead cells was minimal compared to the number of live cells.

Chondrocyte Encapsulation

Figure 14:
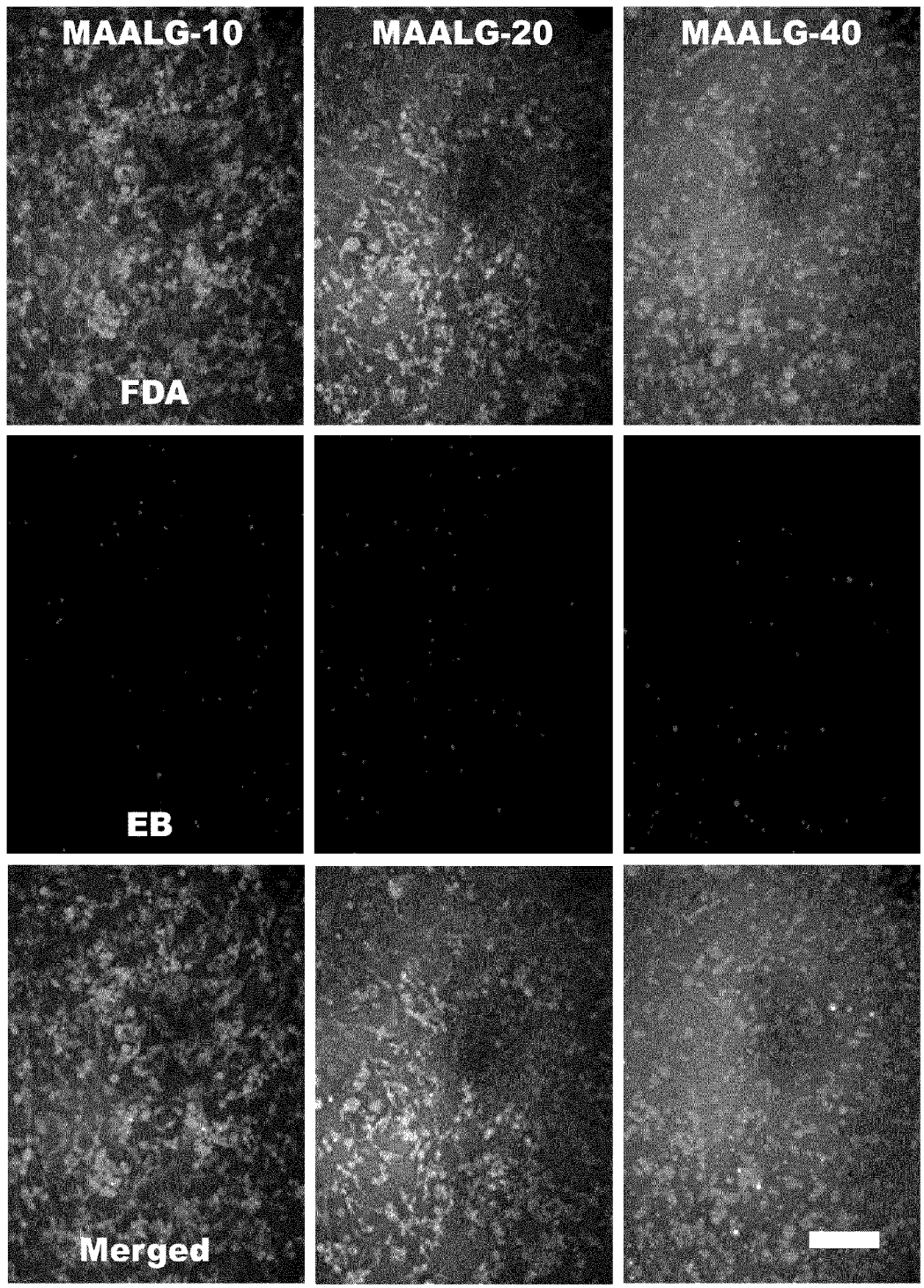
FIG. 14 is a series of fluorescence micrographs showing live (FDA) and dead (EB) encapsulated bovine chondrocytes in various photocrosslinked alginate hydrogels cultured in vitro for 7 days (scale bar indicates 200 µm)

Bovine chondrocytes were photoencapsulated within MAALG-8, MAALG-14, and MAALG-25 hydrogels. The viability of the photoencapsulated chondrocytes in the alginate hydrogels was evaluated by MTS and Live/Dead assays to examine cell survival during the photocrosslinking process and in culture. There were no significant differences in absorbances for the MTS assay between the MAALG-8, MAALG-14, and MAALG-25 conditions immediately following photoencapsulation (0.495±0.017, 0.499±0.019, 0.496±0.023, respectively) or after 7 days in 3-D culture (0.525±0.006, 0.511±0.026, 0.502±0.026, respectively). In addition, a high cell viability (>~80%) was observed throughout all alginate hydrogel compositions at 7 days (FIG. 14) using the Live/Dead assay.

Cell Attachment and Morphology

Few chondrocytes seeded on the surface of MAALG-25 hydrogels were able to adhere (0.06±0.022%), and those that did adhere showed a viability of 48±4.7% after 2 days of culture. All of the adherent cells exhibited a spherical morphology and none spread on the surface of the hydrogels.

Example 2

Synthesis of Methacrylated Heparin

Methacrylated heparin was prepared by reacting heparin (Mw 17000, Sigma, St. Louis, Mo. USA) with 2-aminoethyl methacrylate (AEMA, Sigma) (FIG. 8). To synthesize the methacrylated heparin with methacrylation of two carboxylic acid groups, heparin (1 g) was dissolved in a buffer solution (1% w/v, pH 6.5) of 50 mM 2-morpholinoethanesulfonic acid (MES, Sigma) containing 0.5 M NaCl. NHS (13.8 mg; Sigma) and EDC (45.1 mg; Sigma) (NHS:EDC=1:2) were added to the mixture to activate the carboxylic acid groups of heparin. After 5 min, AEMA (21.7 mg) (molar ratio of NHS:EDC:AEMA=1:2:1) was added to the product. The reaction was maintained at room temperature for 24 hours. After the reaction, the mixture was precipitated by pouring into an excess of acetone, dried under reduced pressure, and rehydrated to a 1% w/v solution in ultrapure deionized water (diH$_2$O) for further purification. The methacrylated heparin was purified by dialysis against diH$_2$O (MWCO 3500; Spectrum Laboratories Inc., Rancho Dominguez, Calif., USA) for 3 days, filtered through a 0.22 μm filter, and lyophilized until dry. To verify the methacrylation of heparin, methacrylated heparin was dissolved in deuterium oxide (Sigma) and placed in an NMR tube. The $^1$H-NMR spectra of the methacrylated heparin was recorded on a Varian Unity-300 (300 MHz) NMR spectrometer (Varian Inc., Palo Alto, Calif., USA) using tetramethylsilane (Sigma) as an internal standard.

Photocrosslinking

Methacrylated alginate was prepared as reported by Jeon, O. et al., *Biomaterials* 30(14):2724-2734 (2009). To fabricate photocrosslinked HP-ALG hydrogels, methacrylated alginate (0.182 g) and methacrylated heparin (0.018 g) were dissolved in 10 ml of diH$_2$O or DMEM with 0.05% w/v photoinitiator (Irgacure-2959, Sigma). These solutions were placed between two glass plates separated by 0.75 mm spacers and photocrosslinked with 365 nm UV light at about 1 mW/cm$^2$ for 10 minutes to form the hydrogels. Photocrosslinked hydrogel disks were created using a 6 mm diameter biopsy punch and placed in diH$_2$O or DMEM.

Mechanical Testing

The elastic moduli of the photocrosslinked HP-ALG hydrogels were determined by performing constant strain rate compression tests using a Rheometrics Solid Analyzer (RSAII, Rheometrics Inc., Piscataway, N.J., USA) equipped with a 10 N load cell. The photocrosslinked HP-ALG hydrogel disks were prepared as described above and maintained in diH$_2$O at 37° C. After 24 hour incubation in diH$_2$O, swollen HP-ALG hydrogel disks were punched once again to form 6 mm diameter disks. Their thickness was measured using calipers, and uniaxial, unconfined compression tests were performed on the hydrogel disks at room temperature using a constant strain rate of 5%/sec. Elastic moduli of photocrosslinked HP-ALG hydrogels were determined from the slope of stress vs. strain plots, limited to the linear first 5% strain of the plots.

Swelling and In Vitro Degradation of HP-ALG Hydrogels

The photocrosslinked HP-ALG hydrogels were lyophilized and dry weights (Wi) were measured. Dried hydrogel samples were immersed in 50 ml of diH$_2$O or DMEM and incubated at 37° C. to reach equilibrium swelling rate. The diH$_2$O or DMEM were replaced every week. Over the course of 8 weeks, samples were removed, rinsed with diH$_2$O, and the swollen (Ws) hydrogel sample weights were measured. The swelling ratio (Q) was calculated by Q=Ws/Wi (n=3 for each time point). After weighing the swollen hydrogels, photocrosslinked HP-ALG hydrogels were lyophilized and weighed (Wd). The percent mass loss was calculated by (Wi−Wd)/Wi×100 (n=3 for each time point).

Release Kinetics of Growth Factors

The kinetics of four different growth factors [basic fibroblast growth factor (FGF-2), vascular endothelial cell growth factor (VEGF), transforming growth factor-beta 1 (TGF-$\beta_1$), and bone morphogenetic protein-2 (BMP-2)] release from HP-ALG hydrogels was determined. Methacrylated alginate (27.3 mg) and methacrylated heparin (2.7 mg) were dissolved in diH$_2$O (1.5 ml) with 0.05% w/v photoinitiator (Irgacure D-2959, Sigma). Each of the four different growth factors (0.75 μg) was added to methacrylated heparin/alginate solution. After gently mixing for 5 minutes, aliquots (300 μl) of solution were placed in 96-well tissue culture plates and photocrosslinked with 365 nm UV light at about 1 mW/cm$^2$ for 10 minutes to form the hydrogels. Each photocrosslinked hydrogel was immersed in 15-ml microcentrifuge tubes containing 10 ml phosphate buffered saline (PBS, pH 7.4) and incubated at 37° C. At various time points, the supernatant was withdrawn and fresh buffer was replenished. The amounts of growth factors in the supernatants were determined with an enzyme-linked immunosorption assay (ELISA) kit (Duoset, R&D Systems, Minneapolis, Minn., USA). ELISA plates were coated with capture monoclonal antibodies and were blocked with bovine serum albumin (1 w/v %) and sucrose (5 w/v %) for 1 hour. After the appropriately diluted samples were added to the ELISA plates, bound growth factors were detected using anti-human polyclonal antibodies. Then, streptavidin-conjugated horseradish peroxidase was added to the plates. The enzyme (peroxidase) and (substrate) tetramethylbenzidine) were added and incubated for 20 minutes. The enzyme reaction was stopped by adding an acidic solution. The absorbance of the samples was read at 450 nm using an ELISA plate reader (SAFIRE, Tecan, Austria). The amounts of growth factors were determined from a calibration curve based on known concentrations of growth factors.

Bioactivity Assay of Growth Factors In Vitro

The bioactivity of BMP-2 released from HP-ALG hydrogels in vitro was assessed by determining its ability to stimulate the ALP activity of MC3T3 preosteoblasts cultured in DMEM containing 10% (v/v) fetal bovine serum at 37° C. with 5% (v/v) CO$_2$. One μg of BMP-2 per hydrogel was loaded into photocrosslinked HP-ALG hydrogels. Cells ($3\times10^4$) were plated in each well of six-well tissue culture plates and the BMP-2 loaded hydrogels were fixed on culture inserts (TRANSWELL, Corning Inc.). The medium was changed every three days. At predetermined time points, the ALP activities were measured. At each time point, cells were lysed by repeating freeze/thaw cycle three times, and the lysates were cleared by centrifugation for 10 minutes at 13000 RPM using an ultracentrifuge. 25 μl of supernatant was incubated with 150 μl of ALP substrate containing p-nitrophenylphosphate (pNPP, Sigma) at 37° C. for 30 minutes. The reaction was stopped by adding 25 μl of 3 N NaOH to the substrate reaction solution. The absorbance of the samples was read at 405 nm using an ELISA plate reader. Each ALP activity measurement was normalized by the protein content, which was measured by the BCA protein assay reagent (Pierce Chemical, Rockford, Ill., USA).

The bioactivities of VEGF released from HP-ALG hydrogels in vitro by determining its ability to stimulate the proliferation of human umbilical vein endothelial cells (HUVECs) cultured in endothelial cell basal medium-2 (EBM-2, Cambrex Bio Science Walkersville, Inc., Walkersville, Md., USA) with 2% (v/v) fetal bovine serum. One μg of VEGF was loaded into HP-ALG hydrogels. Cells ($1\times10^5$ per well) were plated in each well of six-well tissue culture plates and the VEGF-loaded hydrogels were fixed on culture inserts (TRANSWELL). The medium was changed every three days. On weeks 1, 2 and 3, cell numbers were measured using a hemacytometer. One μg of VEGF was loaded into heparin lacking alginate hydrogels served as a comparative group. As a comparative group, VEGF in free form was added into a HUVEC culture in EBM-2 at the concentration of 100 ng/ml. HUVECs cultured in endothelial cell growth medium (EGM-2) or EMB-2 without VEGF served as a positive or negative control, respectively.

In Vivo Bone Formation

All animal procedures were carried out in accordance with a protocol approved by the Institutional Animal Care and Usage Committee. Fifteen male scid mice (ICRSC, 3-4 weeks old; Taconic City, USA) were divided into three groups and anesthetized with xylazine (20 mg/kg) and ketamine (100 mg/kg). Small incisions were made on the dorsal skins of mice. Two pouches per animal were made by blunt dissection in subcutaneous sites, and BMP-2 (1 μg)-loaded photocrosslinked HP-ALG hydrogel disks were immediately implanted into the pouches (n=10). Subsequently, the skin was closed with 6-0 silk sutures (Ethicon, Lenneke Marelaan, Belgium). Eight weeks after the implantation, the rats were sacrificed and the implants were retrieved. Five implants were used for histological analysis, and the others were used for a calcium content assay. The histological specimens were fixed in formalin, embedded in paraffin, sectioned at a thickness of 4 μm, and examined with hematoxylin and eosin staining and Goldner's trichome staining. The bone formation area was measured using an image analysis system (KS400, Zeiss, Munich, Germany) coupled to a light microscope. The bone formation area was expressed as the percentage of bone area in total cross-sectional area [(bone area/total area)×100%]]. The amount of calcium deposited in the implants was measured as previously described.

Statistical Analysis

All quantitative data were expressed as the mean±standard deviation. Statistical analysis was performed with one-way analysis of variance (ANOVA) with Tukey honestly significantly difference post hoc test using Origin software. A value of $p<0.05$ was considered statistically significant.

Synthesis and Characterization of Methacrylated Heparin and Photocrosslinked HP-ALG Hydrogel To prepare photocrosslinked HP-ALG hydrogel, methacrylates were introduced into the heparin main chains as shown in FIG. 8. The $^1$H-NMR spectra of methacrylated heparin exhibit peaks of vinyl methylene and methyl protons that were newly formed by the reaction with AEMA are located at δ6.2, 5.7, and 1.9, respectively.

DMEM or diH$_2$O-equilibrated HP-ALG and alginate hydrogel disks exhibited no significant differences in gross morphologies or size change between two groups after 24 hrs equilibrium.

Elastic Moduli, Swelling Kinetics, and Degradation of the Photocrosslinked HP-ALG Hydrogel To compare mechanical properties between photocrosslinked HP-ALG hydrogel and alginate hydrogel, constant strain-rate compression tests were performed on the alginate hydrogels after 24 hours equilibrium in DMEM or diH$_2$O. There was no significant difference in compressive modulus between the two groups as shown in FIG. 15A.

The swelling ratio change of the alginate hydrogels measured over time reflects changes in their physical and chemical structure. Swelling ratios of these hydrogels in DMEM are shown in FIG. 15B. Both hydrogels displayed rapid swelling after 2 hours, and slightly increased up to 8 weeks. The swelling of the photocrosslinked HP-ALG and normal alginate hydrogels reached equilibrium stage within 48 hours, increased up to 1 and 2 weeks, respectively, then gradually decreased in diH$_2$O (FIG. 15C). Compared to the normal alginate hydrogel, photocrosslinked HP-ALG hydrogel exhibited slower swelling kinetics. The mass loss (%) of photocrosslinked HP-ALG hydrogels over time was determined as a measure of degradation. The mass loss of the photocrosslinked HP-ALG and normal alginate hydrogels were fairly similar regardless of methacrylated heparin addition in DMEM (FIG. 15D). However, in $diH_2O$, photocrosslinked HP-ALG hydrogels showed slower mass loss than alginate hydrogel (FIG. 15E).

Release Kinetics

The release profiles of growth factors from photocrosslinked HP-ALG hydrogels were determined using ELISA and compared with those from photocrosslinked alginate hydrogel. The release of growth factors from the photocrosslinked alginate hydrogels was more rapid than that of photocrosslinked HP-ALG hydrogel delivery system. Almost all of the growth factors were released from the photocrosslinked alginate hydrogels within the first 7 days. In contrast, the release of growth factors from the photocrosslinked HP-ALG hydrogels was slower and sustained over three weeks (FIGS. 16A-D).

Bioactivity of Growth Factors Released from Photocrosslinked HP-ALG Hydrogel

Figure 17A:
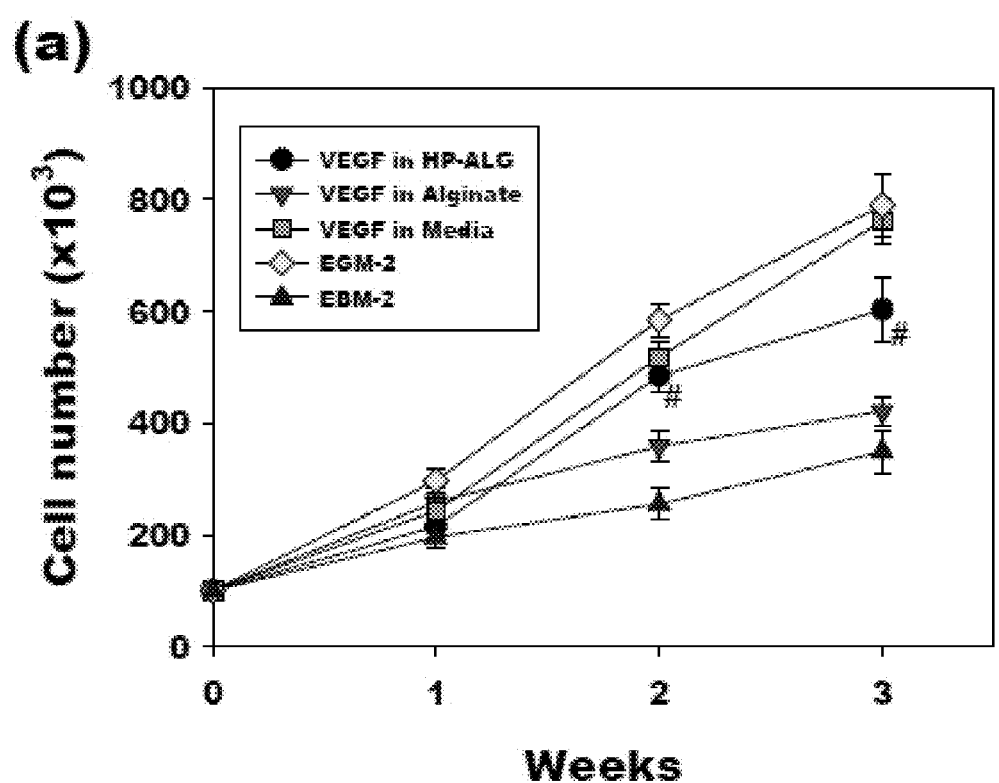
FIGS. 17A-B are plots showing the bioactivities of VEGF (FIG. 17A) and BMP-2 (FIG. 17B) released from the delivery systems, as assessed by measuring HUVEC proliferation and ALP activity of MC3T3 preosteoblasts cultured with the delivery systems, respectively (p<0.05 compared to EGM-2 or VEGF in alginate hydrogel group; *p<0.05 compared to only HP-ALG hydrogel or DMEM group)

To determine whether the growth factors released from photocrosslinked HP-ALG hydrogel are bioactive, the biological activity of the VEGF was evaluated by measuring its ability to stimulate the growth of HUVECs in medium containing delivery system. The HUVECs showed the lowest cell growth in the basal medium without VEGF. VEGF-loaded normal alginate hydrogel slightly improved HUVEC growth compared to the basal medium. Moreover, VEGF-loaded photocrosslinked HP-ALG hydrogel significantly improved HUVEC growth compared to VEGF-loaded normal alginate hydrogel. The cell growth for 3 weeks in VEGF-loaded photocrosslinked HP-ALG hydrogel was not different from that in the EGM (FIG. 17A). This indicates that the VEGF released from photocrosslinked HP-ALG hydrogel for up to 3 weeks was bioactive.

Figure 17B:
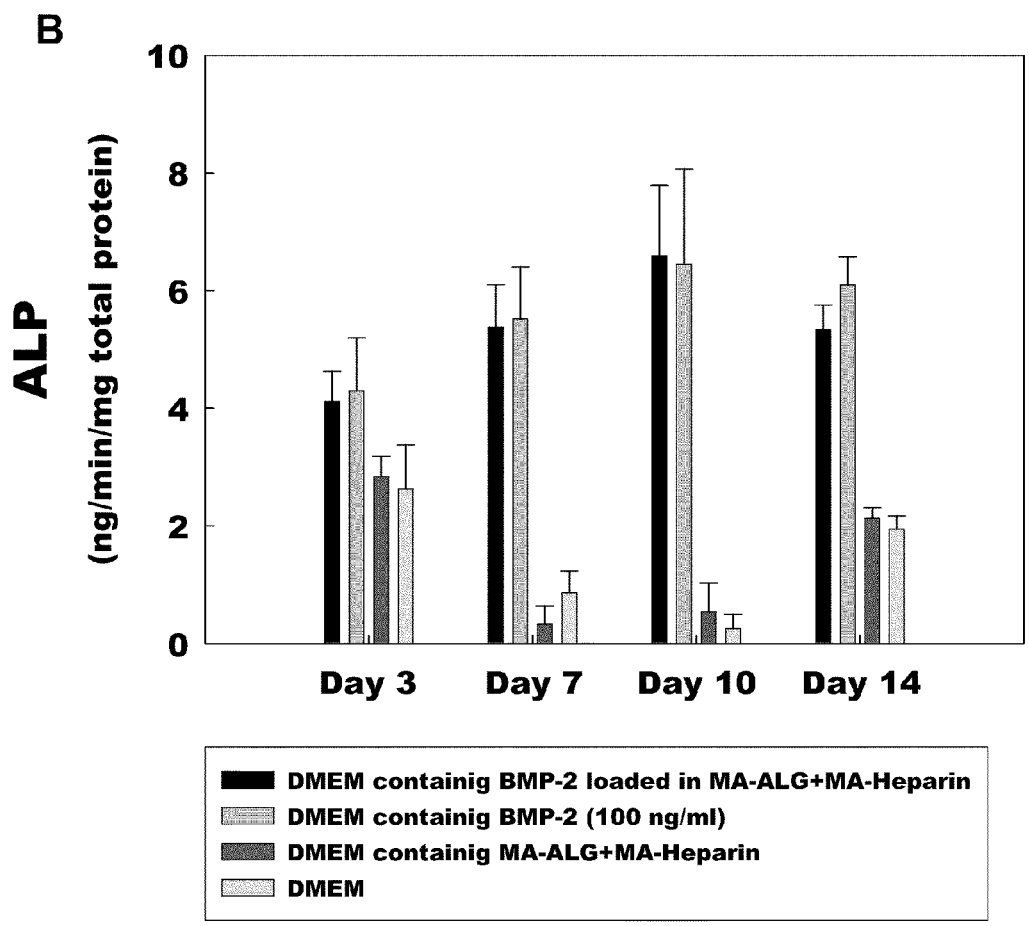

The biological activity of the BMP-2 released from HP-ALG hydrogel was also evaluated by measuring its ability to stimulate the ALP activity of MC3T3 preosteoblast culture in a medium containing the delivery system. The ALP activity of MC3T3 cells did not increase over the entire culture period for photocrosslinked HP-ALG hydrogel without BMP-2. The addition of BMP-2 in a free form to the culture medium enhanced the ALP activity over the entire culture period. The ALP activities for BMP-2-loaded photocrosslinked HP-ALG hydrogel were not different from that of BMP-2 addition to the medium (FIG. 17B). This indicates that the BMP-2 released from photocrosslinked HP-ALG hydrogel was bioactive.

Ectopic Bone Formation

The delivery of BMP-2 using photocrosslinked HP-ALG hydrogel enhanced ectopic bone formation compared to the delivery of BMP-2 using photocrosslinked alginate hydrogel. Histological analysis showed no evidence of bone formation in the photocrosslinked HP-ALG hydrogel without BMP-2. Implantation of BMP-2-loaded photocrosslinked alginate hydrogel induced moderate bone formation. Importantly, BMP-2-loaded photocrosslinked HP-ALG hydrogel induced bone formation to a much greater extent than did BMP-2-loaded photocrosslinked alginate hydrogel (FIGS. 18A-B).

The bone formation area and calcium deposition in the implants were higher in the BMP-2-loaded photocrosslinked HP-ALG hydrogel than in the BMP-2-loaded photocrosslinked alginate hydrogel at eight weeks after implantation (FIGS. 19A-B). The bone formation area and calcium deposition in the photocrosslinked HP-ALG hydrogel without BMP-2 were far less than those in the other groups (FIGS. 19A-B).

Example 3

Preparation of RGD-Modified Methacrylated Alginate

RGD-modified methacrylated alginate was synthesized in a two-step reaction utilizing standard carbodiimide chemistry (FIG. 3). Low molecular weight of sodium alginate (37,000 g/mol) was prepared by irradiating Protanal LF 20/40 (196,000 g/mol, FMC Biopolymer, Philadelphia, Pa., USA) at a gamma dose of 5 Mrad. Twenty-five percent actual methacrylation of alginate carboxylic groups was performed as described in Jeon, O. et al., *Biomaterials* 30(14):2724-2734 (May 2009). Methacrylated alginate solutions (1 w/v %) were prepared with 50 mM of 2-(N-morpholino)ethanesulfonic acid hydrate (MES, Sigma, St. Louis, Mo., USA) buffer solution containing 0.5 M NaCl (Sigma) at pH 6.5, and sequentially mixed with N-hydroxysuccinimide (NHS, Sigma) and 1-ethyl-3-[3-(dimethylamino)propyl]carbodiimide (EDC, Sigma). The molar ratio of NHS to EDC was 0.5:1.0, and the weight ratio of EDC to methacrylated alginate was 1.0:20.7. The amino acid peptide sequence of SEQ ID NO: 1 (Commonwealth Biotechnologies, Richmond, Va.) was added to the methacrylated alginate solution at a weight ratio of 10 mg/g methacrylated alginate. After reacting for 24 h at 4° C., the reaction was stopped by addition of hydroxylamine (0.18 mg/ml, Sigma), and the solution was purified by dialysis against $diH_2O$ (MWCO 3500; Spectrum Laboratories Inc., Rancho Dominguez, Calif., USA) for 3 days, treated with activated charcoal (0.5 mg/100 ml, 50-200 mesh, Fisher, Pittsburgh, Pa.) for 30 min, filtered (0.22 μm filter), and lyophilized. Control methacrylated alginate was prepared in same manner but without the presence of peptide.

Characterization of RGD-Modified Methacrylated Alginate

To verify the RGD-modification of the methacrylated alginate, an $^1$H-NMR spectra of RGD-modified methacrylated alginate was recorded. RGD-modified methacrylated alginate was dissolved in deuterium oxide (Sigma) and placed in an NMR tube. The $^1$H-NMR spectrum of the RGD-modified methacrylated alginate was recorded on a Varian Unity-300 (300 MHz) NMR spectrometer (Varian Inc., Palo Alto, Calif., USA) using tetramethylsilane (TMS) as internal standard. To analyze the degree of peptide modification, a ninhydrin assay was performed. Briefly, RGD-modified methacrylated alginate was dissolved in 5 ml of 1 M sodium acetate buffer (pH 5) and ninhydrin reagent was added. The mixture was kept in boiling water for 20 min. After incubation, 75 ml of a $diH_2O$/absolute ethanol mixture (1/1, v/v) was added and the reaction mixture was cooled to room temperature for 2 h in complete darkness. Ninhydrin reacted with free amino groups and created a water-soluble blue compound. The amount of free amino groups in the RGD-modified methacrylated alginate was determined by measuring the UV absorbance of the supernatant at 570 nm. Methacrylated alginate and glycine were used as the control and the standard, respectively.

Photocrosslinking

To fabricate photocrosslinked RGD-modified alginate or unmodified hydrogels, RGD-modified methacrylated alginate (0.2 g) or unmodified methacrylated alginate (0.2 g) were dissolved in DMEM or $diH_2O$ (10 ml) with 0.05% w/v photoinitiator (Irgacure D-2959, Sigma) for ultimate placement in DMEM or $diH_2O$, respectively. The alginate solutions were injected between two glass plates separated by 0.75 mm spacers and photocrosslinked with 365 nm UV light (Model ENF-260C, Spectroline, Westbury, N.Y.) at about 1 mW/cm$^2$ for 10 min to form the hydrogels. Photocrosslinked hydrogel disks were created using a 6 mm diameter biopsy punch and placed in DMEM or diH$_2$O for swelling and degradation studies, mechanical testing, and culture of cells on the hydrogel surfaces.

Swelling and Degradation of Hydrogels

The photocrosslinked RGD-modified or unmodified alginate hydrogels were lyophilized and dry weights ($W_i$) were measured. Dried hydrogel samples were immersed in 50 ml of DMEM or diH$_2$O and incubated at 37° C. to reach equilibrium swelling state. The DMEM or diH$_2$O was replaced every three days. Over the course of 8 weeks, samples were removed from the DMEM or diH$_2$O, and the swollen ($W_s$) hydrogel sample weights were measured. The swelling ratio (Q) was calculated by $Q=W_s/W_i$ (N=3 for each time point). After weighing the swollen hydrogel samples, the samples were lyophilized and weighed ($W_d$). The percent mass loss was calculated by $(W_i-W_d)/W_i \times 100$ (N=3 for each time point).

Mechanical Testing

The elastic moduli of the photocrosslinked RGD-modified and unmodified alginate hydrogels were determined by performing constant strain rate compression tests using a Rheometrics Solid Analyzer (RSAII, Rheometrics Inc., Piscataway, N.J., USA) equipped with a 10 N load cell. The photocrosslinked RGD-modified and unmodified alginate hydrogel disks were prepared as described in the photocrosslinking section and maintained in DMEM or diH$_2$O at 37° C. After 24 h incubation, swollen alginate hydrogel disks were punched once again to form 6 mm diameter disks, their thickness was measured using calipers, and uniaxial, unconfined compression tests were performed on the hydrogel disks at room temperature using a constant crosshead speed of 5%/sec. Elastic moduli of photocrosslinked alginate hydrogels were determined from the slope of stress vs. strain plots, limited to the first 5% of strain (N=3).

Cell Culture on the Alginate Hydrogels

Chondrocytes (passage number 2) isolated from bovine articular cartilage as reported by Paige, K. T. et al., *Plast Reconstr Surg.* 96(6):1390-1398 (November 1995) were seeded on photocrosslinked RGD-modified or unmodified alginate hydrogel disks in DMEM containing 10% fetal bovine serum (FBS) at a seeding density of $1 \times 10^4$ cells/cm$^2$ in 24-well tissue culture plates and allowed to adhere for 4 hrs in a humidified incubator at 37° C. with 5% CO$_2$. The photocrosslinked RGD-modified or unmodified alginate disks were then transferred to new plates containing fresh media and cultured. The viability and morphology of adhered cells on the RGD-modified or unmodified alginate disks were examined by Live/Dead assay system (Sigma) comprised of fluorescein diacetate (FDA) and ethidium bromide (EB). FDA stains the cytoplasm of viable cells green, while EB stains the nuclei of non-viable cells orange-red. The staining solution was freshly prepared by mixing 1 ml of FDA solution (1.5 mg/ml of FDA in dimethyl sulfoxide) (Research Organics Inc., Cleveland, Ohio) and 0.5 ml of EB solution (1 mg/ml of EB in PBS) with 0.3 ml of PBS (pH 8). At predetermined time points, 20 µl of staining solution was added into each well and incubated for 3-5 min at room temperature, and then stained hydrogel-cell constructs were examined using fluorescence microscopy.

Encapsulation of Chondrocytes

Chondrocytes (passage number 2) were photoencapsulated in RGD-modified or unmodified alginate hydrogels by suspension in RGD-modified or unmodified methacrylated alginate solution (2% w/v in DMEM) with 0.05% w/v photoinitiator. The cell/macromer solutions (300 µl) were pipetted into 96-well tissue culture plates ($1 \times 10^7$ cells/ml) and photocrosslinked with UV for 10 minutes. The resulting hydrogel-cell constructs were removed from the wells, placed in new 24-well tissue culture plates with 1 ml of fresh DMEM, and cultured in a humidified incubator at 37° C. with 5% CO$^2$ for 6 weeks. The viability of encapsulated chondrocytes in the photocrosslinked RGD-modified alginate hydrogels was investigated by a Live/Dead assay (N=3 for each time point).

Biochemical Assays for DNA Content and GAG Production

At each time point, hydrogel-cell constructs were removed from media, homogenized and digested in papain buffer solution (Sigma, 25 µg/ml papain, 2 mM cystein, 50 mM sodium phosphate, 2 mM EDTA, pH 6.5 in nuclease-free water) at 65° C. for 3 h. Hoechst 33258 dye (0.1 µg/ml in nuclease free water, Acros Organics, Morris Plains, N.J.) was used for the DNA assay as described by Solorio, L. D. et al., *J Biomed Mater Res A*. (Mar. 25, 2009). Calf Thymus DNA standards (Rockland Immunochemicals, Gilbertsville, Pa.) were prepared with 0-4 µg/ml DNA in nuclease free water. After the centrifugation of papain-digested samples, 100 µl of supernatants was mixed with 100 µl of the prepared dye solution. Fluorescence intensity of the dye-conjugated DNA solution was measured in 96-well plates on a fluorometer (358 nm excitation and 452 nm emission, SAFIRE, Tecan, Austria), and the DNA content was calculated from a standard curve generated with calf thymus DNA. GAG content was measured using the standard dimethylmethylene blue (DMMB, Sigma) assay in 96-well plates as described by Enobakhare, B. O. et al., *Anal Biochem.* 243(1):189-191 (Dec. 1, 1996). In each well, 50 µl of digest was mixed with 250 µl of dye containing 16 mg/L DMMB and 3.04 g/L glycine (pH 1.5). The absorbance was read at 595 nm using the plate reader (SAFIRE). Chondroitin-6-sulfate (Sigma) from shark cartilage was used to construct the standard curve.

Encapsulation of Chondrocytes and TGF-$\beta_1$

An in vitro TGF-$\beta_1$ release study was performed to examine the time course of TGF-$\beta_1$ release from photocrosslinked RGD-modified alginate hydrogels. TGF-$\beta_1$ (0.75 µg, Pepro-Tech, Rochy Hill, N.J.) was added to RGD-modified methacrylated alginate solution (1.5 ml, 2 w/v % in diH$_2$O). After gently mixing for 5 min, aliquots (300 µl) of solution were placed in 96-well tissue culture plates and photocrosslinked with 365 nm UV light at ~1 mW/cm$^2$ for 10 min. Each photocrosslinked hydrogel was immerged in 15-ml microcentrifuge tubes containing 10 ml PBS and incubated at 37° C. (N=5). At predetermined time points, the supernatant was withdrawn and fresh buffer was replenished. The amount of TGF-$\beta_1$ in the supernatants was determined using an enzyme-linked immunosorption assay (ELISA) kit (Human TGF-$\beta_1$ Duoset, R&D Systems, Minnepolis, Minn., USA). TGF-$\beta_1$ loaded photocrosslinked unmodified alginate hydrogels was used as a comparative group (N=5).

Photocrosslinked RGD-modified unmodified alginate hydrogel-cell constructs containing TGF-$\beta_1$ (100 ng/hydrogel) were prepared in 96-well tissue culture plates as described above, removed from the wells, placed in new 24-well tissue culture plates with 1 ml of fresh DMEM, and cultured in a humidified incubator at 37° C. with 5% CO$_2$ for 6 weeks (N=3). As a control, hydrogel-cell constructs without TGF-$\beta_1$ were cultured in DMEM containing 10 ng/ml TGF-$\beta_1$ (N=3). The medium was changed every three days. At predetermined time points, Live/Dead, GAG, and DNA assays were performed as described above.

Statistical Analysis

All quantitative data is expressed as mean±standard deviation. Statistical analysis was performed with one-way analysis of variance (ANOVA) with Tukey honestly significant difference post hoc test using Origin software (OriginLab Co., Northampton, Mass.). A value of p<0.05 was considered statistically significant.

Preparation and Characterization of Cell Adhesion Peptide-Modified Methacrylated Alginate While alginate hydrogels provide space and mechanical support for tissue regeneration, in their native form they do not provide a mechanism for encapsulted cells to interact and receive important signaling information via adhesion. To partially mimic the cell adhesion capacity of native ECM, a widely used approach is to chemically incorporate specific cell adhesion ligands, such as the ubiquitous cell adhesion peptide sequence of SEQ ID NO: 1 (i.e., RGD) (Rowley, J. A. et al., *Biomaterials* 20(1):45-53 (January 1999); Burdick, J. A. et al., *Biomaterials* 23(22):4315-4323 (November 2002); Massia, S. P. et al., *Anal Biochem.* 187(2):292-301 (June 1990)), which is present in numerous ECM molecules such as fibronectin, collagen and laminin (Bernard, M. P. et al., *Biochemistry-Us* 22(5):1139-1145 (1983); Pierschbacher, M. D. et al., *J Biol Chem.* 257(16):9593-9597 (1992)). In this study, peptides containing the RGD sequence were covalently coupled onto the methacrylated alginate main chains in order to prepare RGD-modified photocrosslinkable and biodegradable alginate hydrogels as shown in FIG. 3. Following alginate methacrylation, the remaining carboxylic acid functional groups along the alginate backbone offered the potential for covalent modification with RGD-containing cell adhesion ligands. $^1$H-NMR spectra of RGD-modified methacrylated alginate macromers exhibit proton peaks that were newly formed by the reaction with peptide, which are located at $\delta$2.75 and 1.7. The proton peaks of vinyl methylene and methyl protons of AEMA are located at $\delta$6.2 and 5.7, and 1.9, respectively. The conjugated RGD concentration was 3.76±0.24 mg/g methacrylated alginate as measured by ninhydrin assay.

Elastic Moduli, Swelling Kinetics, and Degradation of the RGD-Modified Photocrosslinked Alginate Hydrogel To examine whether peptide modification has an effect on photocrosslinked hydrogel mechanical properties, constant strain-rate compression tests were performed after 24 hrs equilibration in DMEM. Representative stress-strain curves of the RGD-modified and unmodified photocrosslinked alginate hydrogels (FIG. 20A) are similar in shape. There was no significant difference in compressive modulus between the two groups (FIG. 20B). These results provide evidence that adhesion peptide modification of methacrylated alginate does not substantially affect the crosslinked structure of photocrosslinked alginate hydrogels because the compressive mechanical response of the hydrogels was unaltered (Zosel, A. et al., *Macromolecules* 26(9):2222-2227 (April 1993)). In addition, the swelling ratio changes and degradation profiles in DMEM were measured to further evaluate whether RGD modification has an effect on the crosslinked structure of the alginate hydrogels. Both RGD-modified and unmodified photocrosslinked alginate hydrogels showed rapid swelling for the first day (FIG. 20C). The swelling of both groups then gradually increased over the course of 8 weeks. The hydrogels exhibited similar swelling kinetics for 4 weeks, and the swelling ratio of the RGD-modified photocrosslinked alginate hydrogels was only slightly higher than that of unmodified alginate hydrogel after 8 weeks. These results also indicate that RGD-modification of methacrylated alginate does not substantially affect the macromolecular structure of photocrosslinked alginate hydrogel over time. The mass loss (%) of alginate hydrogels over time was determined as a measure of degradation (FIG. 20D). The degradation of photocrosslinked RGD-modified alginate hydrogels was slightly faster than that of unmodified alginate hydrogels at 2 and 4 weeks, but there was no difference between the two groups at 8 weeks. These properties were also quantified for the hydrogels in ultrapure deionized water (diH$_2$O). (FIGS. 21A-B).

Characterization of 2D and 3D Chondrocyte Cultures

Bovine chondrocytes were seeded onto RGD-modified and unmodified photocrosslinked alginate hydrogels to evaluate if the peptide modification would enhance chondrocyte adhesion and proliferation. Chondrocytes adhered to the surfaces of RGD-modified hydrogels by 4 hours (data not shown) and exhibited substantial spreading by 7 days. Few chondrocytes seeded on the surfaces of unmodified hydrogels were able to adhere, and those that did remained rounded through 7 days. These results indicate that the chondrocyte cell adhesion and spreading were mediated by the immobilized adhesion ligands (Alsberg, E. et al., *P Natl Acad Sci USA* 99(19): 12025-12030 (Sep. 17, 2002); Ji, J. et al., *Biomaterials* 25(10):1859-1867 (May 2004); Park, K. M. et al., *Macromolecular Research* 16(6):517-523 (August 2008)). Chondrocytes were then photoencapsulated within RGD-modified or unmodified photocrosslinked alginate hydrogels to provide a 3D culture environment which more closely resembles native cartilage tissue. To examine cell survival during the photocrosslinking process and during culture, the viability of the photoencapsulated chondrocytes in the alginate hydrogels was evaluated by a Live/Dead assay. High cell viability was observed throughout all alginate hydrogel compositions for 6 weeks. Chondrocytes in native cartilage are located in lacunae surrounded by ECM (Verdonk, P. C. M. et al., *Osteoarthr Cartilage* 13(7):548-560 (July 2005). ECM-cell interactions promote chondrocyte aggregation (Cao, L. et al., *Matrix Biol.* 18(4):343-355 (August 1999), reduce the level of chondrocyte apoptosis (Shakibaei, M. et al., *J Biol Chem.* 276(16): 13289-13294 (April 2001), and are essential for chondrocyte proliferation, differentiation, survival, and maintenance of chondrogenic activity (Svoboda, K. K. H., *Microsc Res Techniq.* 43(2):111-122 (October 1998); Grashoff, C. et al., *Embo Rep.* 4(4):432-438 (April 2003). The DNA content of RGD-modified hydrogel group was significantly greater than that of unmodified hydrogel group, indicating that RGD modification promoted chondrocyte proliferation in alginate hydrogels. DNA content also significantly increased over time in both groups. After 2 and 4 weeks of culture, chondrocytes photoencapsulated in the RGD-modified alginate hydrogels produced significantly more glycosaminoglycan (GAG), one of the major constituents of cartilage ECM (Wang, D. A. et al., *Nat. Mater.* 6(5):385-392 (May 2007), normalized to DNA content as compared to cells in the unmodified alginate hydrogels. No difference was present at 6 weeks. This result demonstrates that regulating chondrocyte-ECM interactions through controlled integrin-adhesion ligand signaling promotes and accelerates the chondrogenic activity of chondrocytes encapsulated in the photocrosslinked alginate hydrogels. This positive effect on chondrogenesis occurred in the absence of any specific soluble chondrogenic factors other than those present in the serum used.

Encapsulation of Chondrocytes and TGF-$\beta_1$

Figure 22:
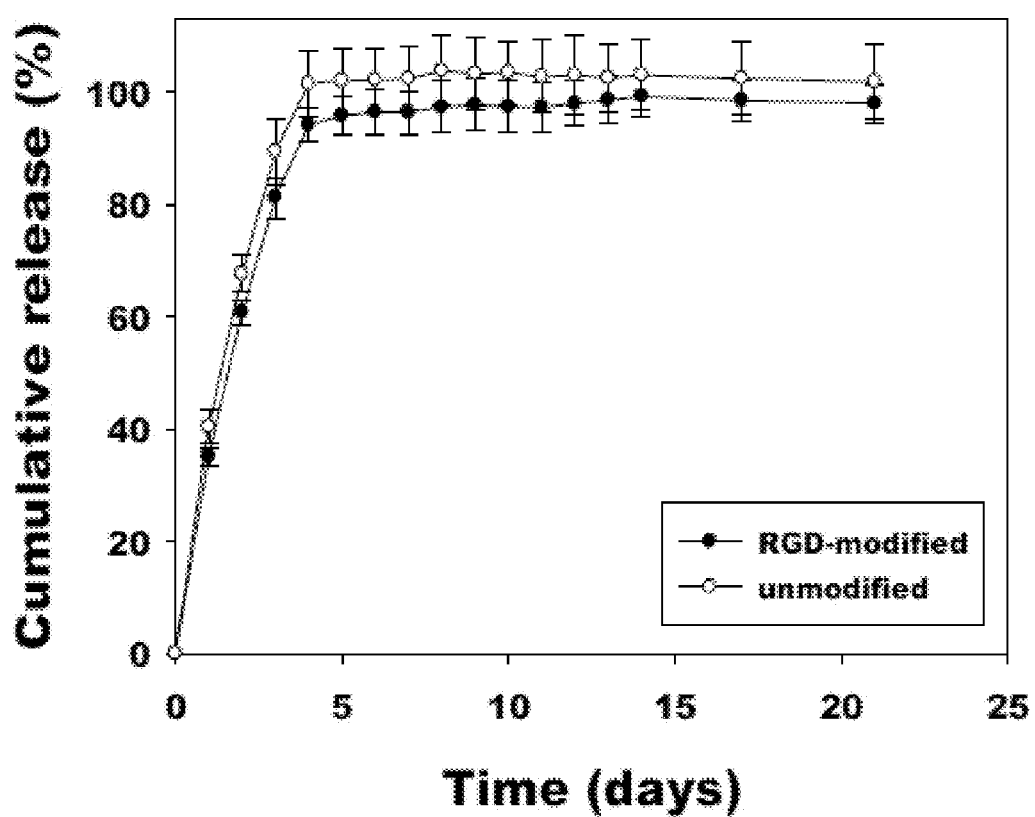
FIG. 22 is a plot showing cumulative release (%) profiles vs. time of TGF-$\beta_1$ from RGD-modified and unmodified photocrosslinked alginate hydrogels (values represent mean±standard deviation)
Figure 23:
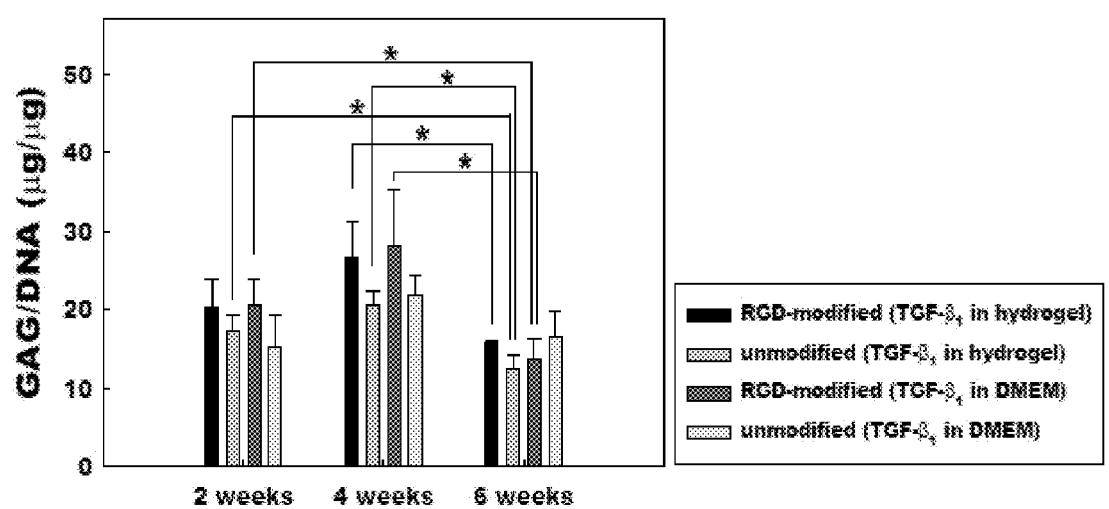
FIG. 23 is a plot showing GAG/DNA contents vs. time for bovine chondrocytes encapsulated with TGF-$\beta_1$ in RGD-modified and unmodified photocrosslinked alginate hydrogels cultured in DMEM and encapsulated bovine chondrocytes without TGF-$\beta_1$ in RGD-modified and unmodified photocrosslinked alginate hydrogels cultured in DMEM containing TGF-$\beta_1$ for 2, 4, and 6 weeks (scale bar indicates 200 µm; *p<0.05).

Growth factors such as TGF-$\beta_1$, which is a member of the TGF-$\beta$ superfamily, are an important part of the soluble biochemical signaling environment which regulate chondrogenesis during development and promote chondrocyte-specific cellular function and cartilaginous ECM production (Kim, S. E. et al., *J Control Release* 91(3):365-374 (September 2003). When chondrocytes are cultured in a three-dimensional environment (e.g., aggregate culture or in a hydrogel), TGF-$\beta_1$ stimulates synthesis of cartilaginous ECM components such as GAG and collagen type II (Lee, J. E. et al., *Biomaterials* 25(18):4163-4173 (August 2004). Therefore, the effect of adhesion ligand modification on the responsiveness of photoencapsulated chondrocytes to TGF-$\beta_1$ delivered either exogenously in the cell culture media (10/ng/ml every 3 days for 6 weeks=140 ng total) or released from the alginate hydrogel itself (100 ng total per hydrogel) was investigated. TGF-$\beta_1$ was released from photocrosslinked RGD-modified and unmodified alginate hydrogels for 4 days at an average release rate of 23.6 and 25.4 ng/hydrogel/day, respectively (FIG. 22). The photoencapsulated chondrocytes exposed to TGF-$\beta_1$ in the alginate hydrogels exhibited high cell viability as observed throughout all construct compositions for 6 weeks using a Live/Dead assay. Chondrogenic activity of the chondrocytes as measured by GAG/DNA content revealed that TGF-$\beta_1$, delivered in the media or from the hydrogels, promoted GAG production per cell (FIG. 23). Similar levels of GAG production were measured when growth factor was delivered via either manner at all time points, even though the release of TGF-$\beta_1$ from the alginate hydrogels was completed within one week and the total amount released was less than that presented exogenously. However, no significant difference in chondrogenic activity was revealed between cells encapsulated in unmodified or RGD-modified alginate hydrogels which were exposed to TGF-$\beta_1$ either in the media or from the hydrogels at all time points. These results indicate that for the specific conditions examined in this study (i.e., peptide type and concentration, TGF-$\beta_1$ concentration), chondrogenic activity of the chondrocytes in the hydrogels was more strongly influenced by the presence of growth factor than controlled ECM-cell interactions.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, the following is claimed:

1. A photocrosslinked biodegradable hydrogel comprising: a plurality of saccharides cross-linked with a plurality of cross-links that are degradable in vivo, the hydrogel being cytocompatible and, upon degradation, producing substantially non-toxic products, wherein the cross-links comprise hydrolyzable acrylate cross-links selected from the group consisting of Formula I

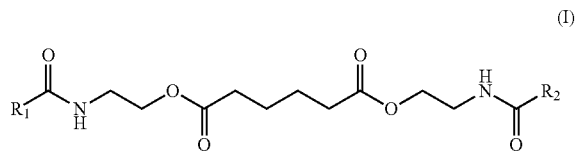

(I)

and Formula II

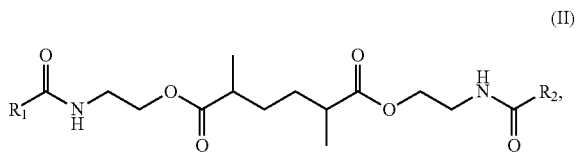

(II)

and wherein $R_1$ and $R_2$ are the same or different saccharides.

2. The photocrosslinked biodegradable hydrogel of claim 1, each of $R_1$ and $R_2$ comprising an alginate main chain.

3. The photocrosslinked biodegradable hydrogel of claim 1, $R_1$ comprising an alginate main chain and $R_2$ comprising a heparin main chain.

4. The photocrosslinked biodegradable hydrogel of claim 1 further including at least one cell dispersed within or on the photocrosslinked biodegradable hydrogel.

5. The photocrosslinked biodegradable hydrogel of claim 4, the at least one cell comprising a progenitor cell.

6. The photocrosslinked biodegradable hydrogel of claim 4 further including at least one attachment molecule to couple the at least one cell to the photocrosslinked biodegradable hydrogel.

7. The photocrosslinked biodegradable hydrogel of claim 6, the at least one attachment molecule being acrylated or methacrylated.

8. The photocrosslinked biodegradable hydrogel of claim 1 further including a bioactive agent that modulates a function and/or characteristic of a cell.

9. The photocrosslinked biodegradable hydrogel of claim 8, the bioactive agent including any agent capable of regulating a cell behavior and/or targeting a specific disease state.

SEQUENCE LISTING

<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Gly Arg Gly Asp Ser Pro
1               5

10. The photocrosslinked biodegradable hydrogel of claim 8, wherein release of the bioactive agent from the hydrogel is dependent on the size and composition of the hydrogel.

11. The photocrosslinked biodegradable hydrogel of claim 1 further including a carrier material dispersed on or within the hydrogel, the carrier material including a bioactive agent for modulating a function and/or characteristic of a cell.

12. The photocrosslinked biodegradable hydrogel of claim 1, the hydrogel comprising a microparticle or a nanoparticle.

13. A photocrosslinked biodegradable hydrogel comprising:
a plurality of saccharides cross-linked with a plurality of hydrolyzable acrylate cross-links that can be hydrolyzed in vivo, the hydrogel being cytocompatible and, upon degradation, producing substantially non-toxic products, wherein the hydrolyzable acrylate cross-links are selected from the group consisting of Formula I

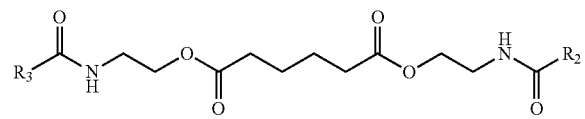

and Formula II

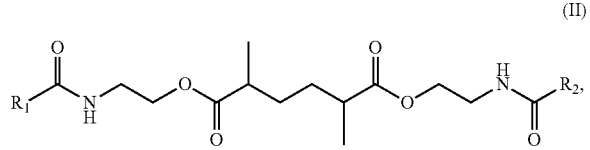

and wherein $R_1$ and $R_2$ are the same or different saccharides.

14. The photocrosslinked biodegradable hydrogel of claim 13 further including at least one cell dispersed within or on the photocrosslinked biodegradable hydrogel.

15. The photocrosslinked biodegradable hydrogel of claim 14 further including at least one attachment molecule to couple the at least one cell to the photocrosslinked biodegradable hydrogel.

16. The photocrosslinked biodegradable hydrogel of claim 13 further including a bioactive agent that modulates a function and/or characteristic of a cell.

17. The photocrosslinked biodegradable hydrogel of claim 16, wherein release of the bioactive agent from the hydrogel is dependent on the size and composition of the hydrogel.

18. The photocrosslinked biodegradable hydrogel of claim 13 further including a carrier material dispersed on or within the hydrogel, the carrier material including a bioactive agent for modulating a function and/or characteristic of a cell.

19. The photocrosslinked biodegradable hydrogel of claim 13, the hydrogel comprising a microparticle or a nanoparticle.

20. A method for forming a photocrosslinked biodegradable hydrogel, the method comprising:
reacting at least one crosslinkable acryl group with at least one saccharide to form a mixture comprising a plurality of acrylated macromers, the acryl group including at least one hydrolyzable linkage;
contacting the mixture with a photoinitiator to initiate cross-linking of the macromers; and
exposing the mixture to a light source to initiate cross-linking of the macromers and thereby form a plurality of saccharides cross-linked with a plurality of hydrolyzable acrylate cross-links selected from the group consisting of Formula I

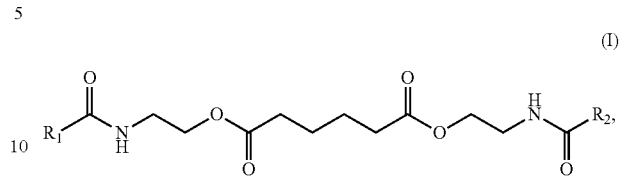

and Formula II

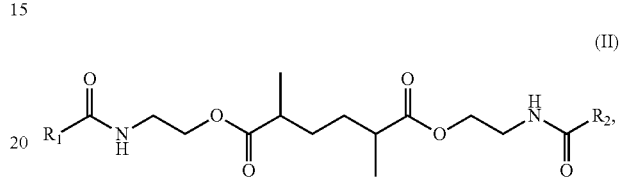

and wherein $R_1$ and $R_2$ are the same or different saccharides.

21. The method of claim 20, further including dispersing at least one cell within or on the photocrosslinked biodegradable hydrogel.

22. The method of claim 21, the hydrogel further including at least one attachment molecule to couple the at least one cell to the photocrosslinked biodegradable hydrogel.

23. The method of claim 20, further including dispersing a bioactive agent in the hydrogel that modulates a function and/or characteristic of a cell.

24. A method for promoting tissue growth in a subject comprising:
administering a photocrosslinked biodegradable hydrogel to a target site in the subject, the hydrogel comprising a plurality of saccharides cross-linked with a plurality of hydrolyzable acrylate cross-links and at least one cell dispersed on or within the hydrogel, the hydrogel being cytocompatible and producing substantially non-toxic products upon degradation, wherein the hydrolyzable acrylate cross-links are selected from the group consisting of Formula I

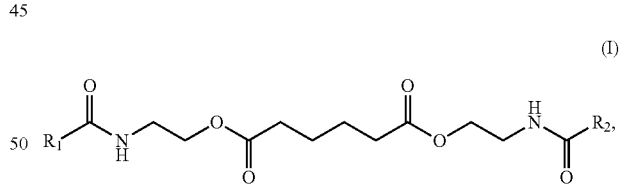

and Formula II

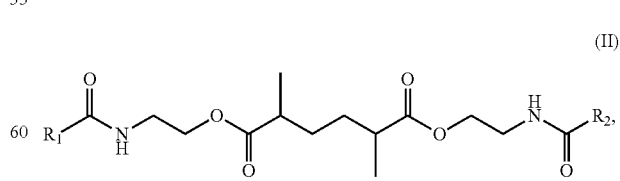

and wherein $R_1$ and $R_2$ are the same or different saccharides.

* * * * *